US010604467B2

(12) United States Patent
Emanuele et al.

(10) Patent No.: US 10,604,467 B2
(45) Date of Patent: Mar. 31, 2020

(54) SOLID FORMS OF CANNABIDIOL AND USES THEREOF

(71) Applicant: Artelo Biosciences, Inc., San Diego, CA (US)

(72) Inventors: R. Martin Emanuele, San Diego, CA (US); Tanise Shattock-Gordon, West Lafayette, IN (US); Tabitha Williford, West Lafayette, IN (US); Mark Andres, West Lafayette, IN (US); Patricia Andres, West Lafayette, IN (US)

(73) Assignee: Artelo Biosciences, Inc., La Jolla, CA (US)

( * ) Notice: Subject to any disclaimer, the term of this patent is extended or adjusted under 35 U.S.C. 154(b) by 0 days.

(21) Appl. No.: 16/396,414

(22) Filed: Apr. 26, 2019

(65) Prior Publication Data

US 2019/0300466 A1     Oct. 3, 2019

Related U.S. Application Data

(63) Continuation of application No. 16/214,913, filed on Dec. 10, 2018, now abandoned.

(60) Provisional application No. 62/597,307, filed on Dec. 11, 2017.

(51) Int. Cl.
| C07D 207/16 | (2006.01) |
| C07D 241/12 | (2006.01) |
| C07C 39/23  | (2006.01) |

(52) U.S. Cl.
CPC ............ *C07C 39/23* (2013.01); *C07D 207/16* (2013.01); *C07D 241/12* (2013.01); *C07B 2200/13* (2013.01); *C07C 2601/16* (2017.05)

(58) Field of Classification Search
CPC .......................... C07D 207/16; C07D 241/12
See application file for complete search history.

(56) References Cited

U.S. PATENT DOCUMENTS

| 4,859,674 A | 8/1989 | Baskin et al. |
| 7,091,205 B2 | 8/2006 | Fu et al. |
| 2006/0276458 A1 | 12/2006 | Chiou |
| 2011/0200531 A1 | 8/2011 | Tan |
| 2017/0079933 A1 | 3/2017 | Whittle et al. |
| 2017/0349518 A1 | 12/2017 | Dickman et al. |

FOREIGN PATENT DOCUMENTS

| WO | 2004/026802 A1 | 4/2004 |
| WO | 2016/127111 A1 | 8/2016 |
| WO | 2019/030158 A1 | 2/2019 |

OTHER PUBLICATIONS

McAllister et al., Mol Cancer Ther 2007; 6(11), pp. 2921-2927.*
Zhang et al., Med Oncol (2012) 29: 534-538.*
Julian Kenyon; Wai Liu and Angus Dalgleish; Report of Objective Clinical Responses of Cancer Patients to Pharmaceutical-grade Synthetic Cannabidiol; Anticancer Research International Journal of Cancer Research and Treatment; Anticancer Research 38: 5831-5835 (2018), all pages.
Pius S. Fasinu, Sarah Phillips, Mahmoud A. Elsohly and Larry A. Walker; Current Status and Prospects for Cannabidiol Preparations as New Therapeutic Agents; Pharmacotherapy vol. 36, No. 7, 2016, pp. 781-796.
Paula Morales, Patricia H. Reggio and Nadine Jagerovic; An Overview on Medicinal Chemistry of Synthetic and Natural Derivatives of Cannabidiol; frontiers in Pharmacology; published Jun. 28, 2017; vol. 8; Article 422; all pages.
Zhao et al., Mechanisms and Clinical Application of Tetramethylpyrazine (an Interesting Natural Compound Isolated from Ligusticum Wallichii): Current Status and Perspective; Hindawi Publishing Corporation; Oxidative Medicine and Cellular Longevity; vol. 2016, Article ID 2124638, 9 pages.

* cited by examiner

*Primary Examiner* — Rebecca L Anderson

(57) ABSTRACT

Disclosed herein are cocrystals of cannabidiol and a coformer containing 5-6 membered rings comprised of carbon and nitrogen atoms, wherein the 5-6 membered rings can be unsaturated or saturated and the rings contain 1 to 2 nitrogen atoms. Cocrystals of cannabidiol and a coformer selected from L-proline, D-proline, tetramethylpyrazine, and 4,4'-dipyridyl are also disclosed herein.

9 Claims, 21 Drawing Sheets

DSC

SOLID FORMS OF CANNABIDIOL AND USES THEREOF

RELATED APPLICATIONS

This patent application is a continuation application of U.S. Ser. No. 16/214,913, filed on Dec. 10, 2018, which claims the benefit of priority to U.S. Ser. No. 62/597,307, filed on Dec. 11, 2017, all of which are incorporated by reference herein in their entireties, including the drawings.

FIELD OF THE INVENTION

The present disclosure is in the field of medicinal cannabis. In particular, the disclosure concerns solid forms of cannabidiol, methods of making such solid forms, pharmaceutical compositions of such solid forms, and uses thereof for various medical treatments.

BACKGROUND OF THE DISCLOSURE

Cannabidiol (CBD) is a compound identified from cannabis that is pharmaceutically active. It is a phytocannabinoid and accounts for up to 40% of a cannabis extract. (Borgelt L M, et al., (2013), *Pharmacotherapy*, 33(2): 195-209; Aizpurua-Olaizola, Oier, et al., (2016), *Journal of Natural Products*, 79(2):324-331; Campos A C, et al., (2012), *Philos. Trans. R. Soc. Lond. B Biol. Sci.*, 367(1607): 3364-78). CBD is also found and isolated from other plants such as, e.g., hemp. CBD can also be produced and isolated by other methods of production including yeast manufacturing (see, WO2016/010827). CBD is presently used clinically in combination with (−)-trans-$\Delta^9$-tetrahydocannabinol ($\Delta^9$-THC) for treatment of neuropathic symptoms associated with multiple sclerosis (Morales et al., (2017) *Front. Pharmacol.* 8:1-18). CBD is also being investigated as a single agent for use as a neuroprotective, treatment of hypoxia-ischemia events, addiction and uses as an anxiolytic, antipsychotic, analgesic, anti-inflammatory, anti-asthmatic, anti-epileptic and anti-cancer agent (Fasinu et al., (2016) *Pharmacotherapy* 36(7):781-796; Fanelli et al., (2017) *J. Pain Res.* 10:1217-1224; Morales et al., (2017) *Front. Pharmacol.* 8:1-18; and Devinsky et al., (2017) *N Engl J Med* 376(21): 2011-20).

Cocrystals are crystalline molecular complexes of two or more non-volatile compounds bound together in a crystal lattice by non-ionic interactions. Pharmaceutical cocrystals are cocrystals of a therapeutic compound, e.g., an active pharmaceutical ingredient (API), and one or more non-volatile compound(s) (referred to herein as coformer). A coformer in a pharmaceutical cocrystal is typically a non-toxic pharmaceutically acceptable molecule, such as, for example, food additives, preservatives, pharmaceutical excipients, or other APIs. A cocrystal of an API is a distinct chemical composition of the API and coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC). As crystalline forms, cocrystals may possess more favorable solid state, physical, chemical, pharmaceutical and/or pharmacological properties or may be easier to process than known forms or formulations of the API. For example, a cocrystal may have different dissolution and/or solubility properties than the API, and can, therefore, be more effective in therapeutic delivery. A cocrystal may also affect other pharmaceutical parameters such as storage stability, compressibility and density (useful in formulation and product manufacturing), permeability, and hydrophilic or lipophilic character. New pharmaceutical compositions comprising a cocrystal of a given API, therefore, may have attractive or superior properties as compared to its natural state or existing drug formulations.

SUMMARY OF THE DISCLOSURE

In one aspect, the disclosure relates to a solid form comprising cannabidiol and the coformer L-proline.

In another embodiment, cannabidiol L-proline solid form has a molar ratio of cannabidiol to L-proline of about 1:1.

In another embodiment, the solid form of cannabidiol L-proline is crystalline.

In another embodiment, the solid form of cannabidiol L-proline is a cocrystal.

In another embodiment, cannabidiol L-proline cocrystal is anhydrous.

In another embodiment, cannabidiol L-proline cocrystal is cannabidiol L-proline Form A.

In another embodiment, cannabidiol L-proline Form A and has an x-ray diffraction pattern (XRPD) comprising one or more peaks at 5.3, 5.8, 9.4, 10.7, 11.1, 11.4, 11.7, 12.3, 15.4, 15.8, 16.4, 17.3, 18.7, 19.2, 19.4, 20.0. 20.8, 21.3, 23.1, and 24.5 degrees 2θ±0.2.

In another embodiment, cannabidiol L-proline Form A has an x-ray powder diffraction pattern substantially similar to FIG. 2.

In another embodiment, cannabidiol L-proline Form A has a DSC thermogram with a peak onset of approximately 146.4° C. or a peak maximum at about 147.8° C.

In another embodiment, cannabidiol L-proline Form A has a DSC thermogram which is substantially similar to the DSC thermogram of FIG. 3.

Another embodiment of the disclosure includes pharmaceutical compositions comprising the aforementioned solid forms of cannabidiol L-proline.

In another embodiment, the pharmaceutical compositions of the solid forms of cannabidiol L-proline further comprise a pharmaceutically acceptable excipient or carrier.

Another aspect of the disclosure includes a solid form comprising cannabidiol and the coformer D-proline.

In an embodiment of this aspect, the solid form of cannabidiol and the coformer D-proline has a molar ratio of cannabidiol to D-proline is about 1:1.

In another embodiment, the solid form of cannabidiol D-proline is crystalline.

In another embodiment the solid form of cannabidiol D-Proline is a cocrystal.

In another embodiment the cocrystal form of cannabidiol D-Proline is cannabidiol D-Proline cocrystal Form A.

In another embodiment, the cocrystal is anhydrous.

In another embodiment, cannabidiol D-Proline Form A has an x-ray diffraction pattern comprising one or more peaks at 5.2, 5.8, 9.4, 10.6, 11.2, 11.5, 12.4, 12.7, 15.3, 15.7, 16.4, 17.4, 18.7, 19.2, 19.4, 20.2, 20.7, 21.2, 23.3, 24.0, 24.6, 25.6, and 26.2 degrees 2θ±0.2.

In another embodiment, cannabidiol D-Proline Form A has an x-ray powder diffraction pattern substantially similar to FIG. 7.

In another embodiment, cannabidiol D-Proline Form A has a DSC thermogram with a peak onset of approximately 154.3° C. or a peak maximum at about 155.5° C.

In another embodiment, cannabidiol D-Proline Form A has a DSC thermogram which is substantially similar to the DSC thermogram of FIG. 8.

Another embodiment of the disclosure includes pharmaceutical compositions comprising the aforementioned solid forms of cannabidiol D-proline.

In another embodiment, the pharmaceutical compositions of the solid forms of cannabidiol D-proline further comprise a pharmaceutically acceptable excipient or carrier.

Another aspect of the disclosure are solid forms comprising cannabidiol and the coformer tetramethylpyrazine.

In an embodiment of this aspect, the cannabidiol tetramethylpyrazine solid form is crystalline.

In another embodiment, the cannabidiol tetramethylpyrazine solid form has a molar ratio of cannabidiol to tetramethylpyrazine that is about 1:1.

In another embodiment, the cannabidiol tetramethylpyrazine solid form is a cocrystal.

In another embodiment, the cannabidiol tetramethylpyrazine cocrystal has an x-ray diffraction pattern comprising one or more peaks at about 9.1, 14.6, 18.3, and 19.6 degrees 2θ±0.2.

In another embodiment, the cannabidiol tetramethylpyrazine cocrystal has an x-ray powder diffraction pattern substantially similar to FIG. 12.

In another embodiment, the cannabidiol tetramethylpyrazine cocrystal has a DSC thermogram with a peak onset of approximately 89.9° C. or a peak maximum at about 92.8° C.

In another embodiment, the cannabidiol tetramethylpyrazine cocrystal has a DSC thermogram which is substantially similar to the DSC thermogram of FIG. 13

Another embodiment of the disclosure includes pharmaceutical compositions comprising the aforementioned solid forms of cannabidiol tetramethylpyrazine.

In another embodiment, the pharmaceutical compositions of the solid forms of cannabidiol tetramethylpyrazine further comprise a pharmaceutically acceptable excipient or carrier.

Another aspect disclosed herein are solid forms comprising cannabidiol and the coformer 4,4'dipyridyl.

In some embodiments, the cannabidiol 4,4'dipyridyl solid form is crystalline.

In some embodiments, the cannabidiol 4,4'dipyridyl solid form is a cocrystal.

In some embodiments, the cannabidiol 4,4'dipyridyl solid form has a molar ratio of cannabidiol to 4,4'dipyridyl that is about 1:1.

In some embodiments, the cannabidiol 4,4'dipyridyl cocrystal is cannabidiol 4,4'dipyridyl cocrystal Material A.

In some embodiments, the cannabidiol 4,4'dipyridyl cocrystal Material A has an x-ray diffraction pattern comprising one or more peaks at about 4.4, 7.7, 8.9, 9.2, 12.0, 15.0, 15.5, 16.3, 17.9, 18.4, 18.6, 18.9, 19.6, 20.3, 20.6, 21.6, 22.6, and 25.6 degrees 2θ±0.2.

In some embodiments, the cannabidiol 4,4'dipyridyl cocrystal Material A has an x-ray powder diffraction pattern substantially similar to FIG. 16.

In some embodiments, the cannabidiol 4,4'dipyridyl cocrystal Material A has a DSC thermogram with a peak onset of approximately 139.6° C. or a peak maximum at about 140.7° C.

In some embodiments, the cannabidiol 4,4'dipyridyl cocrystal Material A has a DSC thermogram which is substantially similar to the DSC thermogram of FIG. 17.

Another aspect disclosed herein is a solid form cannabidiol 4,4'dipyridyl Material B.

In some embodiments, cannabidiol 4,4'dipyridyl Material B has an x-ray diffraction pattern comprising peaks at about 7.7, 9.2, 10.6, 11.1, 11.9, 15.2, 16.2, 18.3, 19.6, 20.4, 20.8, 22.1, 22.3, 24.1 degrees 2θ±0.2 degrees 2θ±0.2.

In some embodiments, cannabidiol 4,4'dipyridyl Material B has an x-ray powder diffraction pattern substantially similar to FIG. 21.

Another embodiment of the disclosure includes pharmaceutical compositions comprising the aforementioned solid forms of cannabidiol 4,4'dipyridyl.

In another embodiment, the pharmaceutical compositions of the solid forms of cannabidiol 4,4'dipyridyl further comprise a pharmaceutically acceptable excipient or carrier.

Another aspect of the disclosure includes methods for treating a disease or condition amenable to treatment with cannabidiol comprising administering one or more of the aforementioned solid forms of cannabidiol to a subject in need of treatment.

In some embodiments the disease or condition is selected from: central nervous system disorders; cardiovascular disorders; neurovascular disorders, cancers (alone or with other cancer agents), such as, without limitation, solid tumors, e.g., anaplastic ependymoma, Diffuse Intrinsic Pontine Glioma (DIPG), Glioblastoma multiforme, bladder, breast, head and neck, prostate, neuroendocrine, Non-Hodgkin's lymphoma, non-small cell lung, colorectal pancreatic, ovarian; reducing adverse effects of other cancer treatments, cancer metastasis; autoimmunity; multiple sclerosis; multiple sclerosis-related muscle spasms; Parkinson's disease; psychosis; epilepsy (convulsions and seizures), including, without limitation, treatment-resistant epilepsy, epilepsy in tuberous sclerosis complex, Dravet syndrome, febrile infection-related epilepsy syndrome (Fires) in the acute and chronic phases, Sturge-Weber Syndrome, status epilepticus, malignant migrating partial seizures, brain tumor-related epilepsy, seizures caused by early onset epilepsy such as Lennox-Gastaut Syndrome; psychiatric disorders; impaired cognitive function, including, without limitation, cognitive impairment in schizophrenia; anxiety; depression; bipolar disorders; inflammation; pain; fibromyalgia; hepatitis; epidermolysis bullosa; spasticity in neurodegenerative diseases; cachexia and anorexia; ocular hypertension in glaucoma; movement disorders, such as, without limitation, dystonic disorders; neuromuscular disorders; Prader Willi syndrome; spasms in Tourette syndrome; pseudobulbar affect; reducing drug dependence, such as without limitation, smoking, and opioid addiction; diabetes mellitus; graph versus host disease (GVHD); atherosclerosis; inflammatory bowel disease; autoimmune disorders, such as, without limitation, thyroid disease, Crohn's disease; ulcerative colitis; systemic lupus erythematosus (SLE); cutaneous lupus erythematosus; psoriasis; autoimmune uveitis; autoimmune hepatitis; rheumatoid arthritis, hypersensitivity lung diseases; hypersensitivity pneumonitis; delayed-type hypersensitivity; Sjogren's disease; acquired immunodeficiency syndrome, sarcoidosis; interstitial lung disease (ILD); scleroderma; dermatitis; use as an anti-oxidant; use as antipsychotic; iritis; conjunctivitis; keratoconjunctivitis; idiopathic bilateral progressive sensorineural hearing loss; aplastic anemia; pure red cell anemia; idiopathic thrombocytopenia; polychondritis; Graves ophthalmopathy; amyotrophic lateral sclerosis (ALS) and symptoms associated with ALS; primary biliary cirrhosis; ileitis; chronic inflammatory intestinal disease; celiac disease; irritable bowel syndrome; Alzheimer's disease; prion associated disease;

fatty liver; sleep disorders, such as, without limitation, insomnia, sleep maintenance sleep disorders in Parkinson's, sleep disorders associated with posttraumatic stress disorder (PTSD); acne; cannabis withdrawal symptoms; OCD; PTSD; nausea, nausea related to cancer treatment; vomiting; emesis; motion sickness; and hypoxia-ischemia (acute stroke).

In some embodiments of the disclosure, a claim may "comprise" an aspect or embodiment. In other aspects or embodiments, a claim may "consist" of an aspect or embodiment. In still other embodiments, a claim may "consist essentially of" an aspect or embodiment.

DETAILED DESCRIPTION OF THE EMBODIMENTS

Cannabidiol (CBD) is a compound having the structure of Formula I:

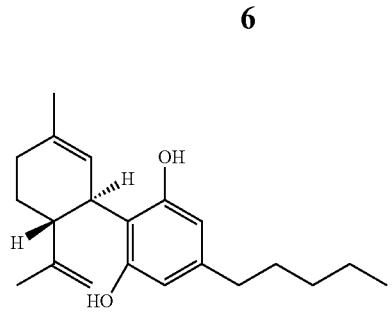

(Formula I)

Disclosed herein are cocrystal forms of cannabidiol wherein the coformers comprise 5-6 member rings comprised of carbon and nitrogen atoms, wherein the rings can be saturated or unsaturated, and wherein the rings contain one or two nitrogen atoms per ring. The rings can be substituted or unsubstituted.

Disclosed herein is a cocrystal of cannabidiol:L-proline in a molar ratio of about 1:1 cannabidiol:L-proline (Form A). The structure of L-proline is shown in Formula II.

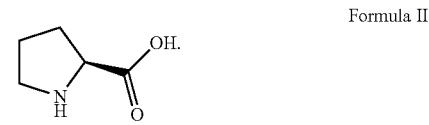

Formula II

In another embodiment, the cannabidiol:L-proline cocrystal is produced as a mixture with CBD when a 2:1 ratio is used.

In another embodiment, the cannabidiol:L-proline Form A cocrystal is anhydrous.

Figure 1:
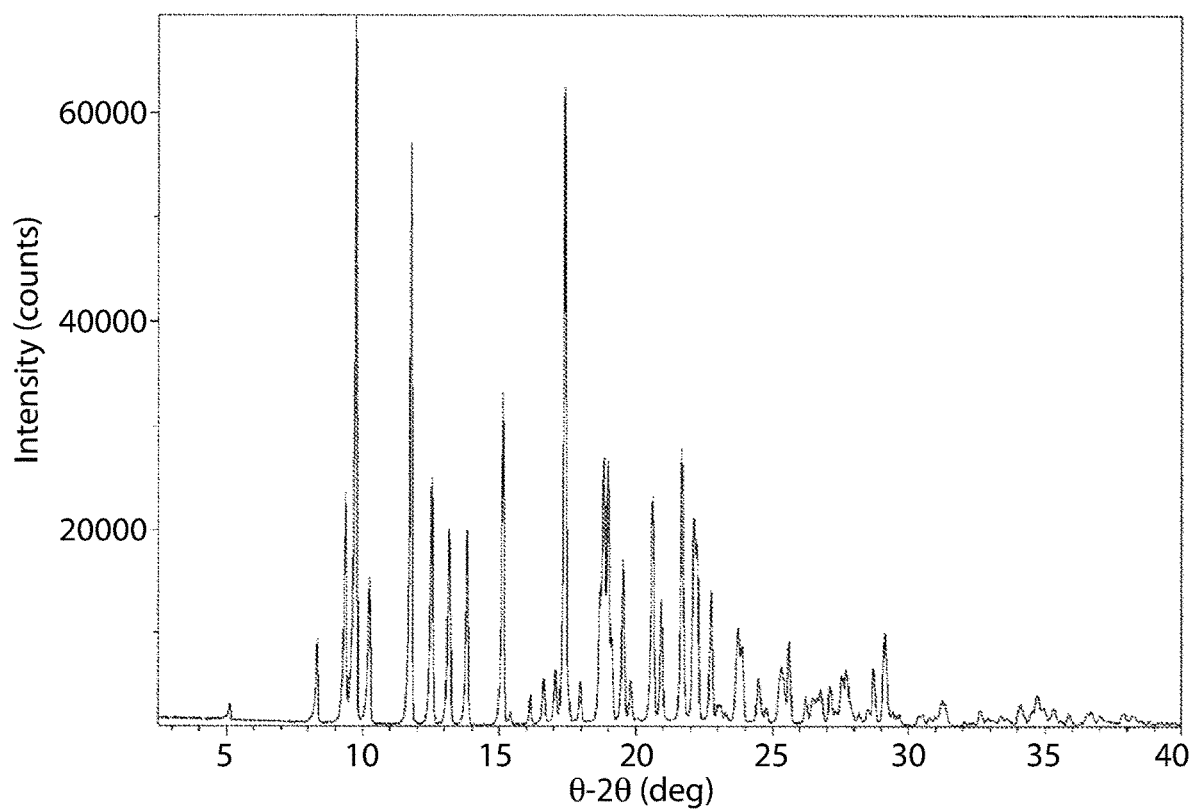
FIG. 1 shows an XRPD pattern of cannabidiol.

The XRPD pattern corresponding to cannabidiol starting material used herein is shown in FIG. 1.

Figure 2:
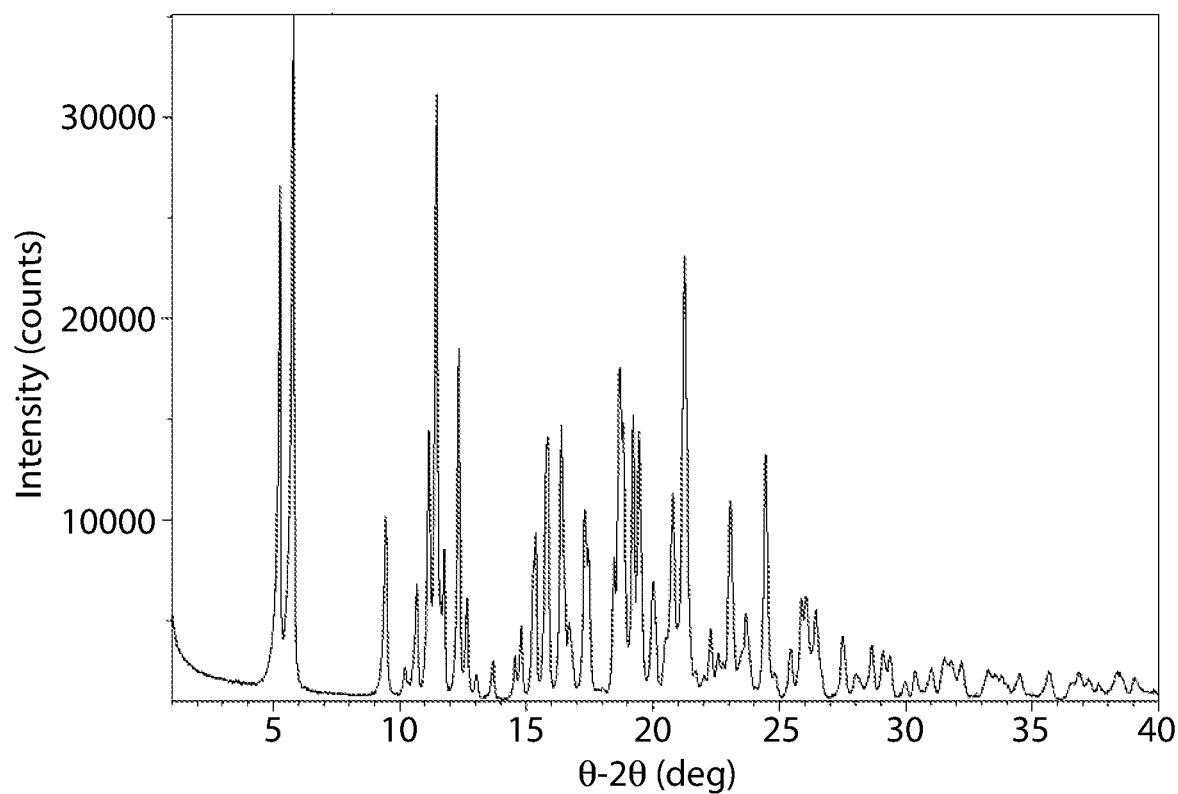
FIG. 2 shows an XRPD pattern of cannabidiol L-proline Form A.

The XRPD pattern corresponding to cannabidiol L-proline (Form A) is shown in FIG. 2. As can be determined, the XPRD pattern of FIG. 2 differs from the XRPD patterns of cannabidiol starting material shown in FIG. 1.

An XRPD pattern substantially the same as the pattern of FIG. 2 may be used to characterize cannabidiol L-proline Form A.

A smaller subset of the peaks identified in FIG. 2 may be used to characterize cannabidiol:L-proline Form A. For example, any one or more of the peaks identified at about °2θ may be used to characterize cannabidiol:L-proline Form A. For example, any one or more of the peaks at about 5.3, 5.8, 9.4, 10.7, 11.1, 11.4, 11.7, 12.3, 15.4, 15.8, 16.4, 17.3, 18.7, 19.2, 19.4, 20.0. 20.8, 21.3, 23.1, or 24.5 degrees 2θ±0.2.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about ±0.2 degrees 2θ. A person skilled in the art, having the benefit of this disclosure, would understand the use of "about" in this context. The term "about" in reference to other defined parameters, e.g., water content, DSC, TGA, IR, NMR, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

As used herein, "substantially the same" in reference to a form exhibiting characteristics similar to, for example, an XRPD pattern, an IR spectrum, a Raman spectrum, a DSC thermogram, TGA thermogram, NMR, SSNMR, etc., indicates that the cocrystal is identifiable by that method and could range from similar to substantially the same, so long as the material is identified by the method with variations expected by one of skill in the art according to the experimental variations, including, for example, instruments used, time of day, humidity, season, pressure, room temperature, etc.

Figure 3:
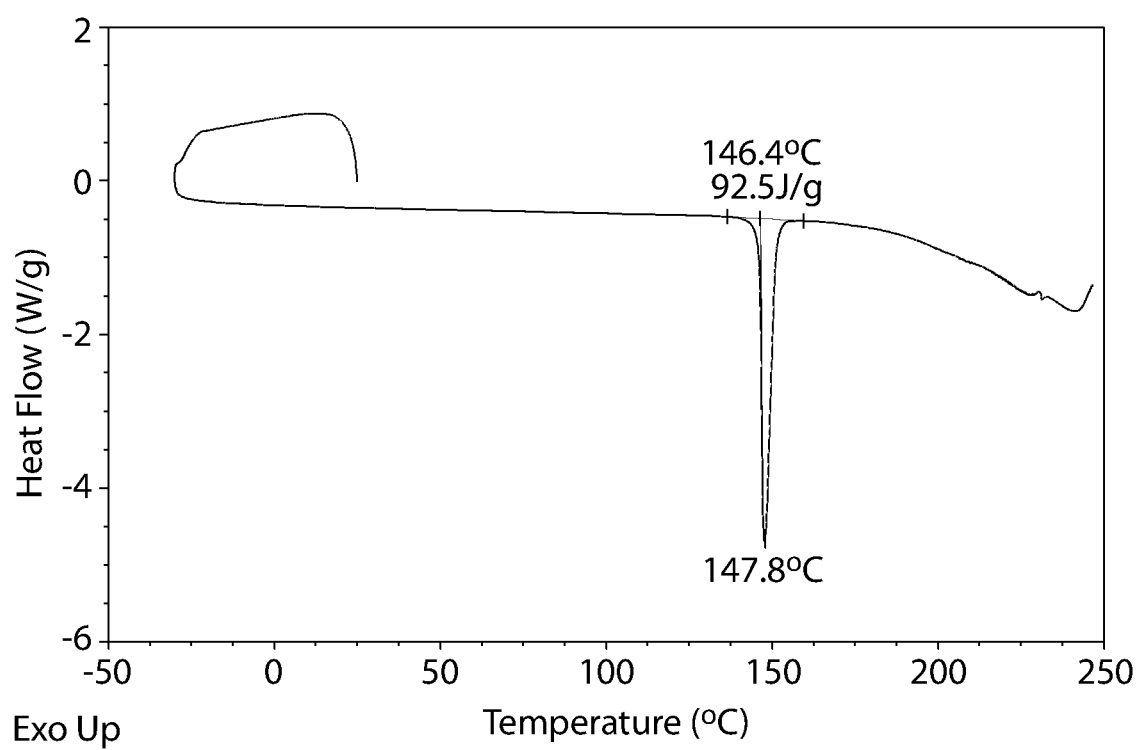
FIG. 3 shows a differential scanning calorimetry thermogram for cannabidiol L-proline Form A.
Figure 4:
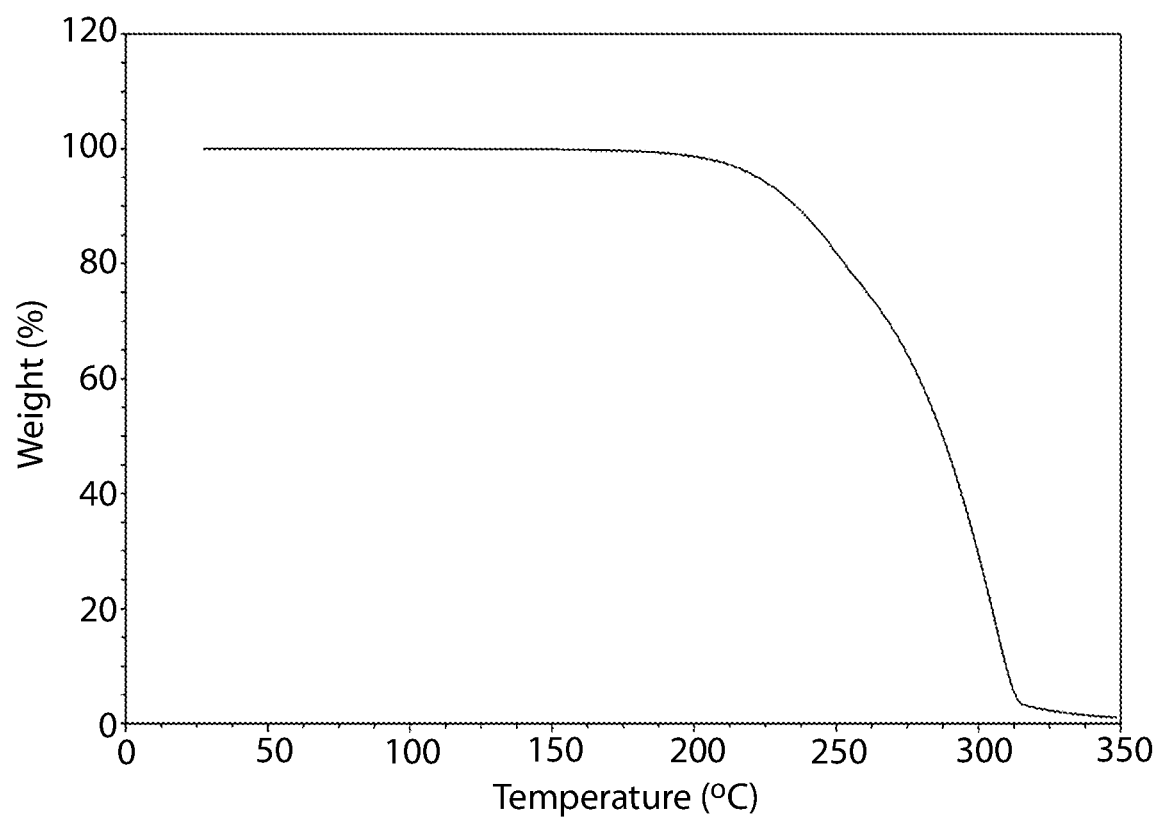
FIG. 4 shows a thermogravimetric thermogram for cannabidiol L-proline Form A.

Cannabidiol L-proline Form A may be characterized by its thermal characteristics. For example, FIG. 3 is a DSC thermogram of Cannabidiol L-proline Form A and shows a single sharp endotherm with an onset at about 146.4° C. and peak maximum at about 147.8° C. No significant weight loss is observed in the TGA thermogram up to the melt (FIG. 4). Cannabidiol L-proline Form A may be characterized by DSC alone or in combination with its XRPD diffraction pattern of FIG. 2 or one or more of the peaks set forth herein.

Figure 5:
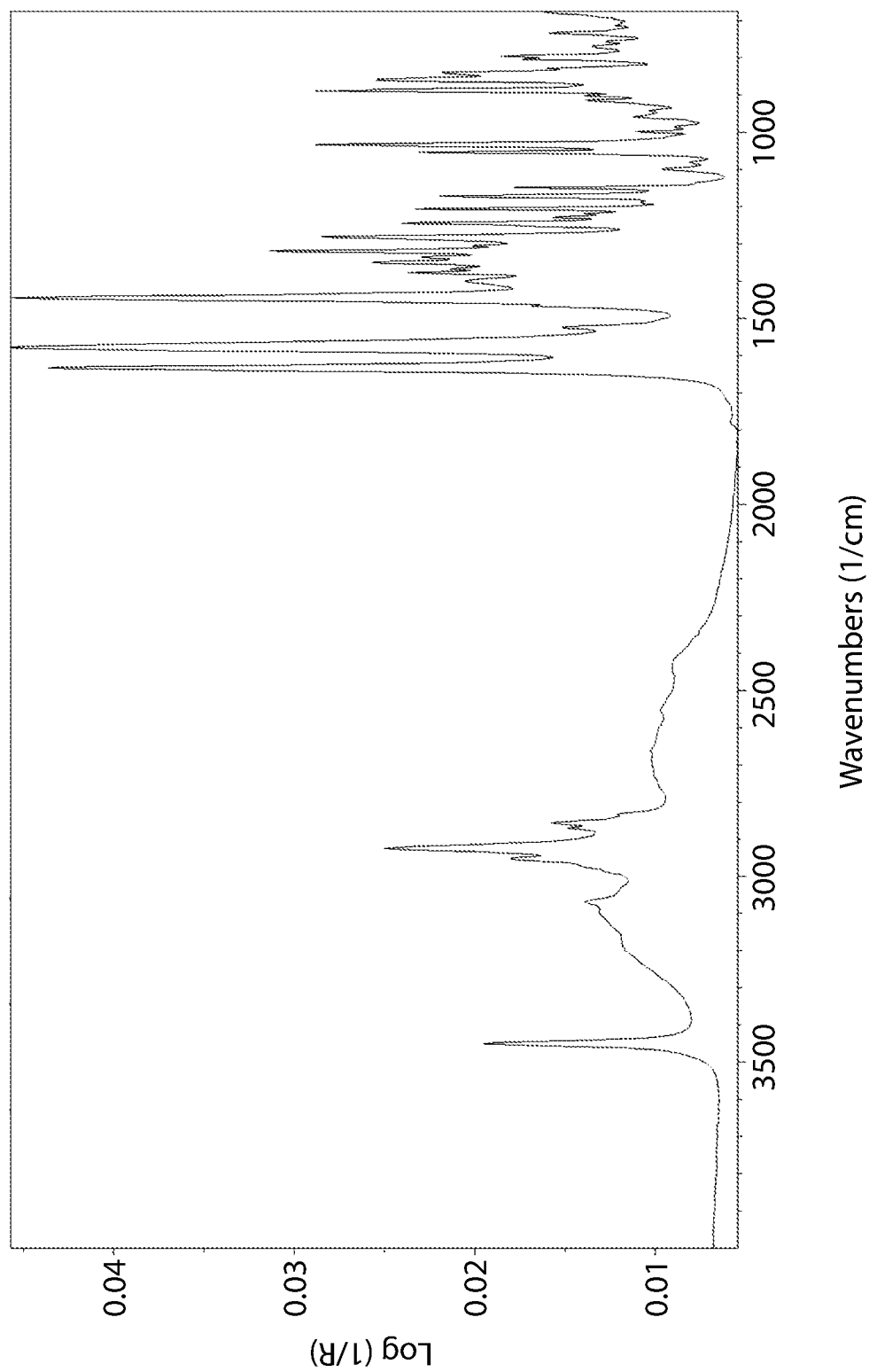
FIG. 5 shows an infrared spectrum of cannabidiol L-proline Form A.

Cannabidiol L-proline Form A may be characterized by the FT-IR spectrum in FIG. 5. When considering just infrared spectroscopy the entire FT-IR spectrum may be used to characterize Form A, or a subset thereof. For example, any one of the peaks at about 3450 or 2900, or others may be used alone or in combination to characterize Cannabidiol L-proline Form A.

Disclosed herein is a cocrystal of cannabidiol:D-proline in a molar ratio of about 1:1 cannabidiol:D-proline. The structure of D-proline is shown in Formula III.

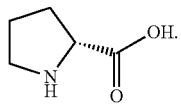

Formula III

Figure 7:
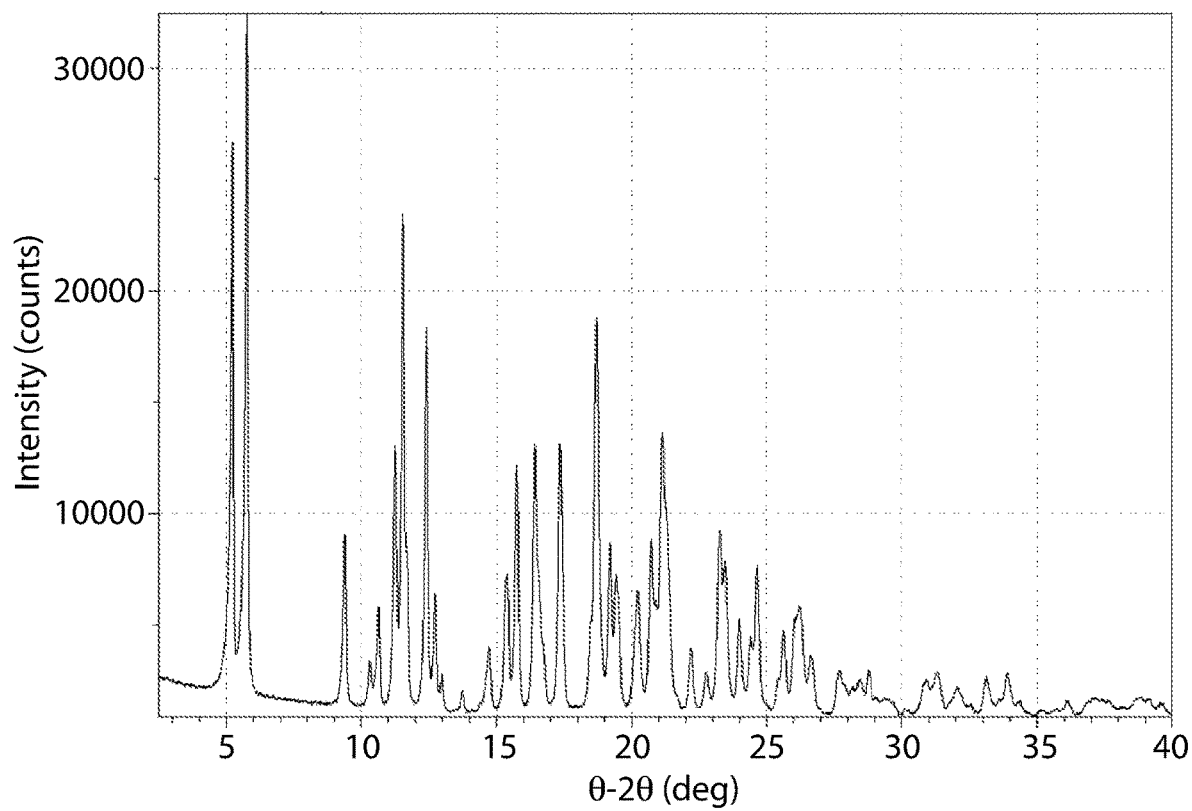
FIG. 7 shows an XRPD pattern of cannabidiol D-proline cocrystal cannabidiol L-proline Form A.

The XRPD pattern corresponding to the coformer D-proline is shown FIG. 7. As can be determined, the XPRD pattern of cannabidiol:D-proline in FIG. 7 differs from cannabidiol starting material of FIG. 1, and Cannabidiol L-proline Form A (FIG. 2).

A pattern substantially the same as the XRPD pattern of cannabidiol D-proline as shown in FIG. 7 may be used to characterize the cocrystal of cannabidiol D-proline Form A. A smaller subset of the peaks identified in FIG. 7 may be used to characterize the cocrystal of cannabidiol D-proline Form A. For example, any one or more of the peaks identified at about °2θ may be used to characterize cannabidiol D-proline Form A. For example, any one or more of the peaks at about 5.2, 5.8, 9.4, 10.6, 11.2, 11.5, 12.4, 12.7, 15.3, 15.7, 16.4, 17.4, 18.7, 19.2, 19.4, 20.2, 20.7, 21.2, 23.3, 24.0, 24.6, 25.6, and 26.2 degrees 2θ±0.2.

Figure 8:
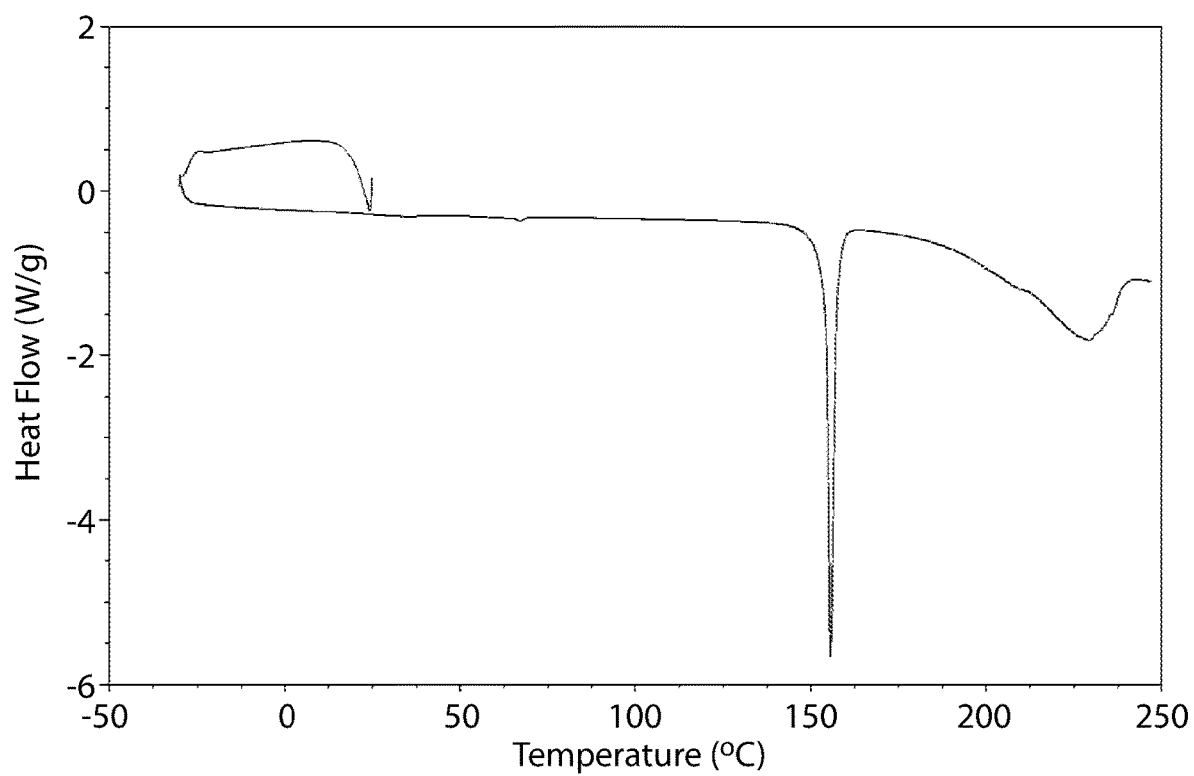
FIG. 8 shows a differential scanning calorimetry thermogram for cannabidiol D-proline cocrystal Form A.
Figure 9:
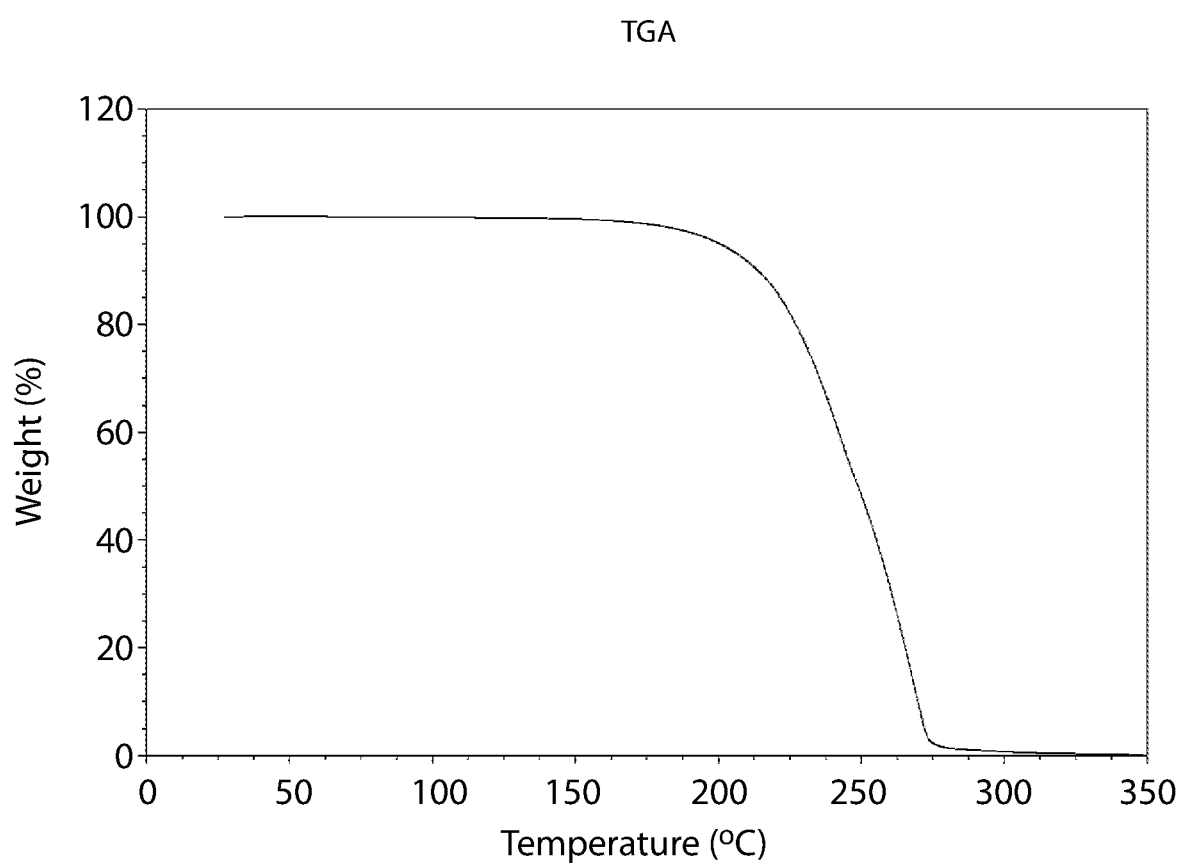
FIG. 9 shows a thermogravimetric thermogram for cannabidiol D-proline cocrystal Form A.

Cannabidiol D-proline Form A may be characterized by its thermal characteristics. For example, FIG. 8 is a DSC thermogram of Cannabidiol D-proline Form A and shows a single sharp endotherm with an onset at about 154.3° C. and peak maximum at about 155.5° C. No significant weight loss is observed in the TGA thermogram up to the melt (FIG. 9). Cannabidiol D-proline Form A may be characterized by DSC alone or in combination with its XRPD diffraction pattern of FIG. 7 or one or more of the peaks set forth herein.

Figure 10:
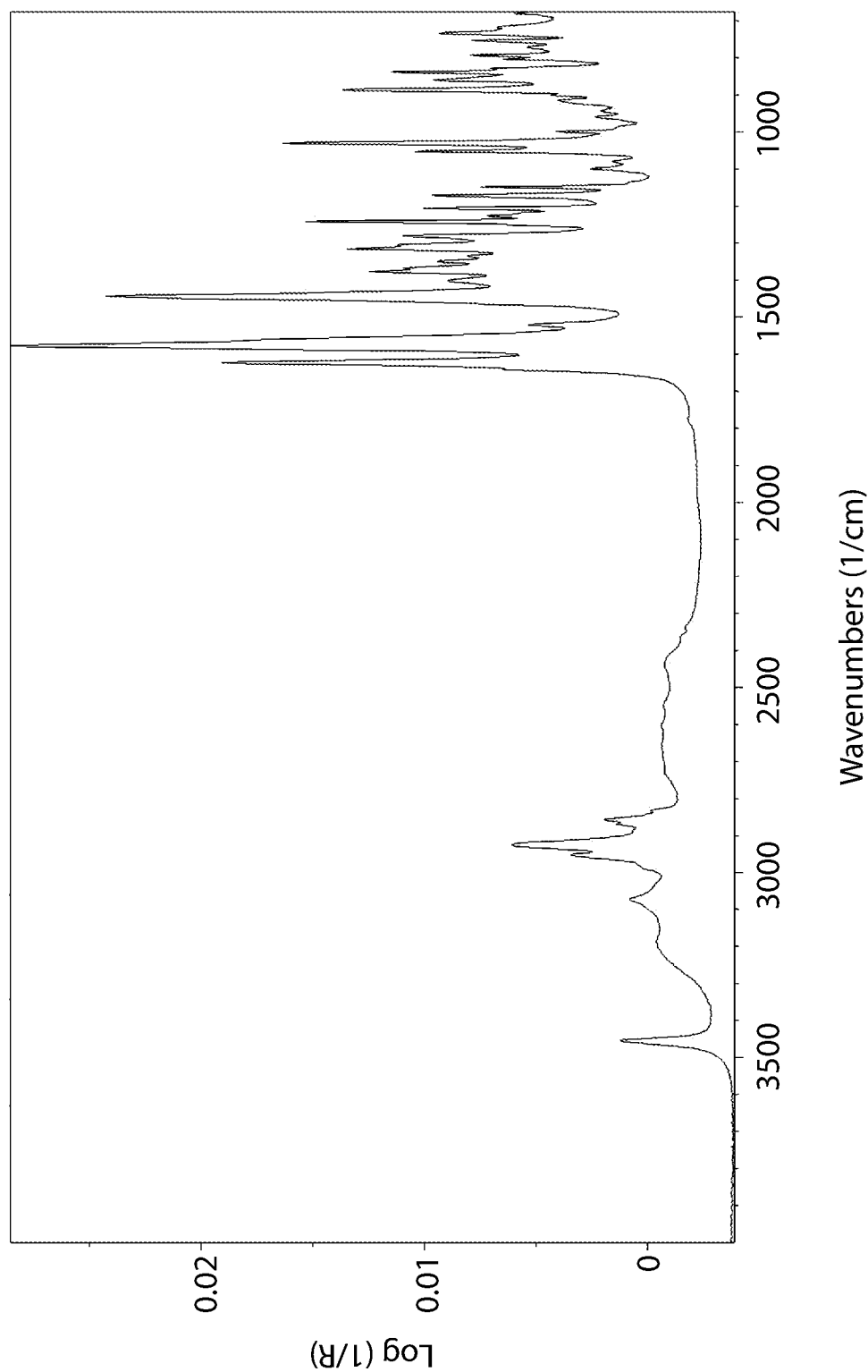
FIG. 10 shows an infrared spectrum of cannabidiol D-proline cocrystal Form A.

Cannabidiol D-proline Form A may be characterized by the FT-IR spectrum in FIG. 10. When considering just infrared spectroscopy the entire FT-IR spectrum may be used to characterize Cannabidiol D-proline Form A, or a subset thereof.

Disclosed herein is a cocrystal of cannabidiol tetramethylpyrazine in a about a molar ratio of 1:1 cannabidiol tetramethylpyrazine. The structure of tetramethylpyrazine is shown in Formula IV.

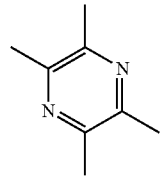

Formula IV

Figure 12:
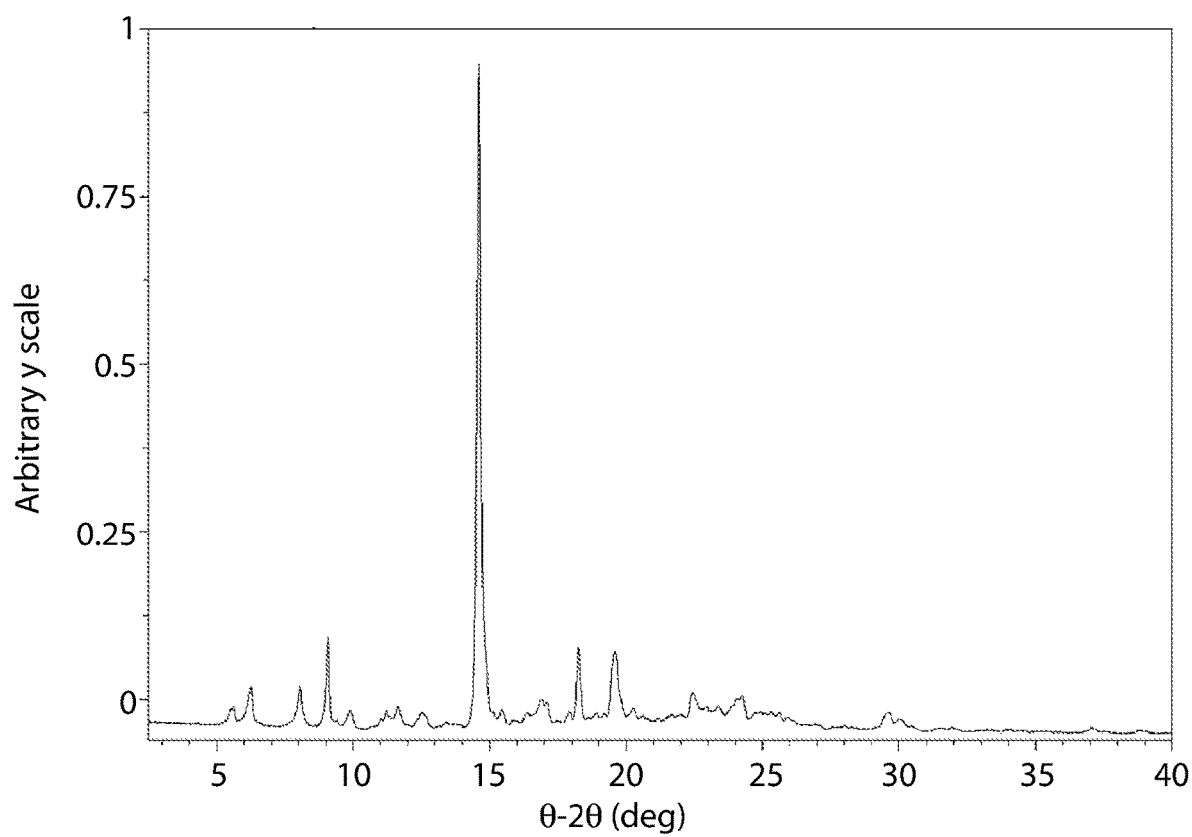
FIG. 12 shows an XRPD pattern for cannabidiol tetramethylpyrazine cocrystal.

The XRPD pattern corresponding to the coformer tetramethylpyrazine is shown FIG. 12. As can be determined, the XPRD pattern of cannabidiol tetramethylpyrazine in FIG. 12 differs from cannabidiol as shown in FIG. 1.

A pattern substantially the same as the pattern of cannabidiol tetramethylpyrazine shown in FIG. 12 may be used to characterize the cocrystal of cannabidiol tetramethylpyrazine. A smaller subset of the peaks identified in FIG. 12 for cannabidiol tetramethylpyrazine may be used to characterize the cocrystal of cannabidiol tetramethylpyrazine. For example, any one or more of the peaks at about 9.1, 14.6, 18.3, and 19.6 degrees 2θ±0.2.

Figure 13:
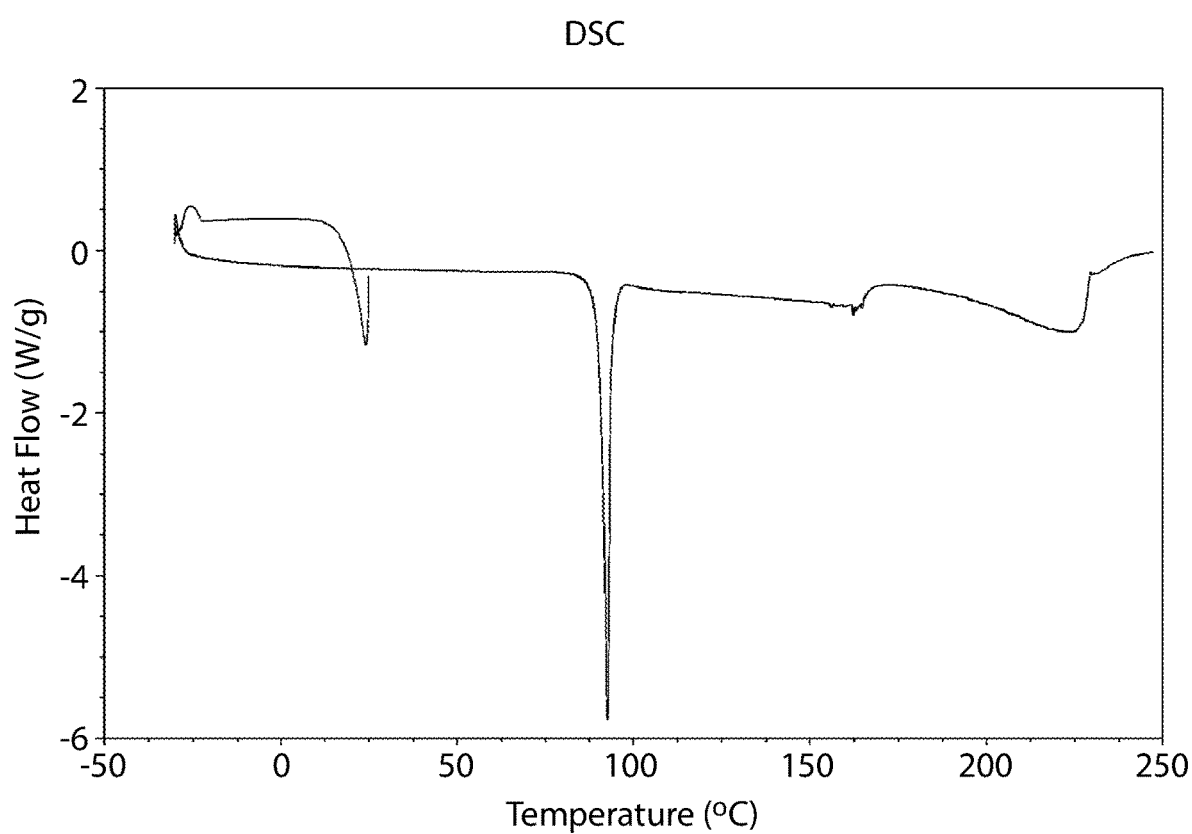
FIG. 13 shows a differential scanning calorimetry thermogram for cannabidiol tetramethylpyrazine cocrystal.

Cannabidiol:tetramethylpyrazine may be characterized by its thermal characteristics. For example, FIG. 13 is a DSC thermogram of cannabidiol:tetramethylpyrazine and shows a single sharp endotherm with an onset at about 89.9° C. and peak maximum at about 92.8° C. Cannabidiol:tetramethylpyrazine may be characterized by DSC alone or in combination with its XRPD diffraction pattern of FIG. 12 or one or more of the peaks set forth herein.

Disclosed herein is a cocrystal of cannabidiol:4,4'-dipyridyl Material A in about a molar ratio of 1:1 cannabidiol:4,4'-dipyridyl. The structure of 4,4'-bipyridyl is shown in Formula V.

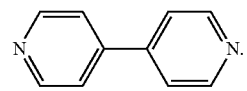

Formula V

Figure 16:
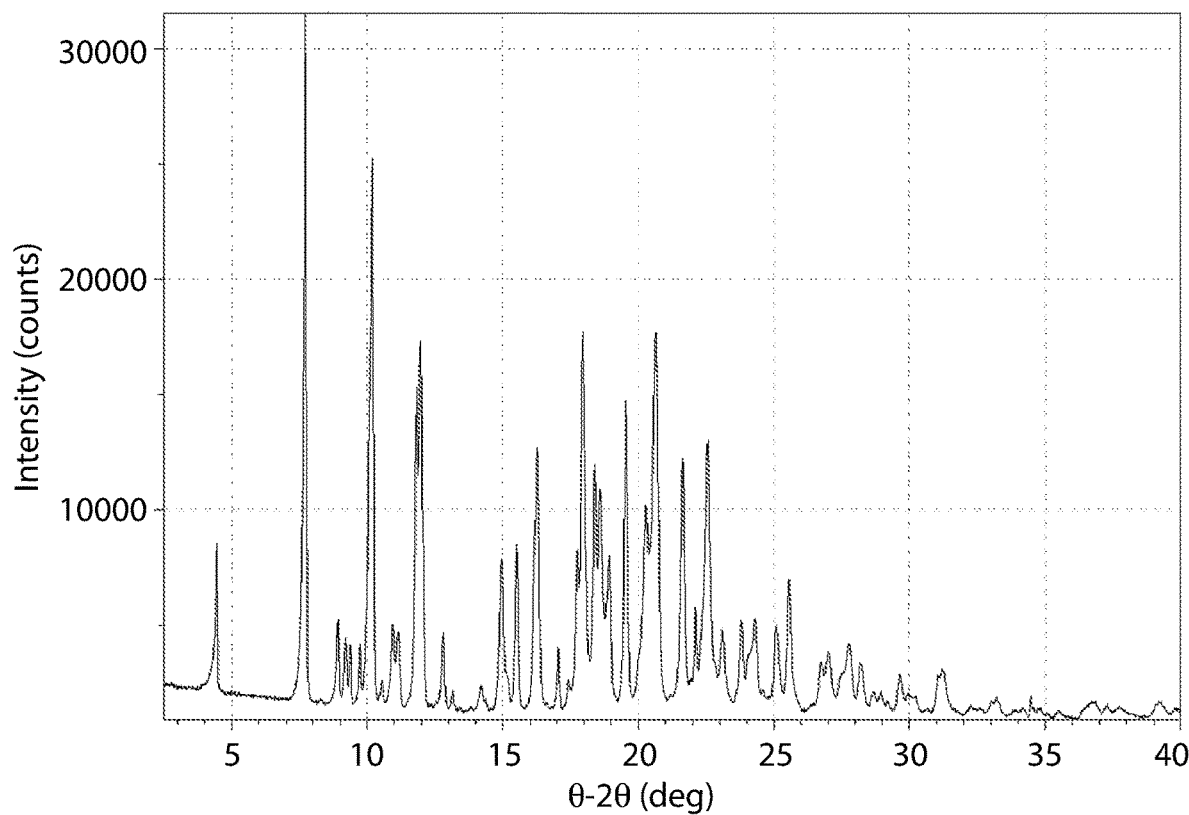
FIG. 16 shows an XRPD pattern for cannabidiol 4,4'-dipyridyl cocrystal Material A.

The XRPD pattern corresponding to the cannabidiol 4,4'-dipyridyl Material A is shown in FIG. 16. As can be determined, the XPRD pattern of cannabidiol 4,4'-dipyridyl Material A in FIG. 16 differs from the XRPD pattern of cannabidiol starting material FIG. 1.

A pattern substantially the same as the pattern of cannabidiol 4,4'-dipyridyl Material A shown in FIG. 16 may be used to characterize the cocrystal of cannabidiol 4,4'-dipyridyl Material A. A smaller subset of the peaks identified for cannabidiol:4,4'-dipyridyl in FIG. 16 may be used to characterize the cocrystal of cannabidiol:4,4'-dipyridyl Material A. For example, any one or more of the peaks identified at about °2θ may be used to characterize the cocrystal of cannabidiol 4,4'-dipyridyl Material A. For example, any one or more of the peaks at about 4.4, 7.7, 8.9, 9.2, 12.0, 15.0, 15.5, 16.3, 17.9, 18.4, 18.6, 18.9, 19.6, 20.3, 20.6, 21.6, 22.6, and 25.6 degrees 2θ±0.2.

Additionally, a unique crystalline material, designated cannabidiol 4,4'-dipyridyl Material B, resulted after cannabidiol 4,4'-dipyridyl Material A was exposed to 95% RH for 1 week at RT.

Figure 21:
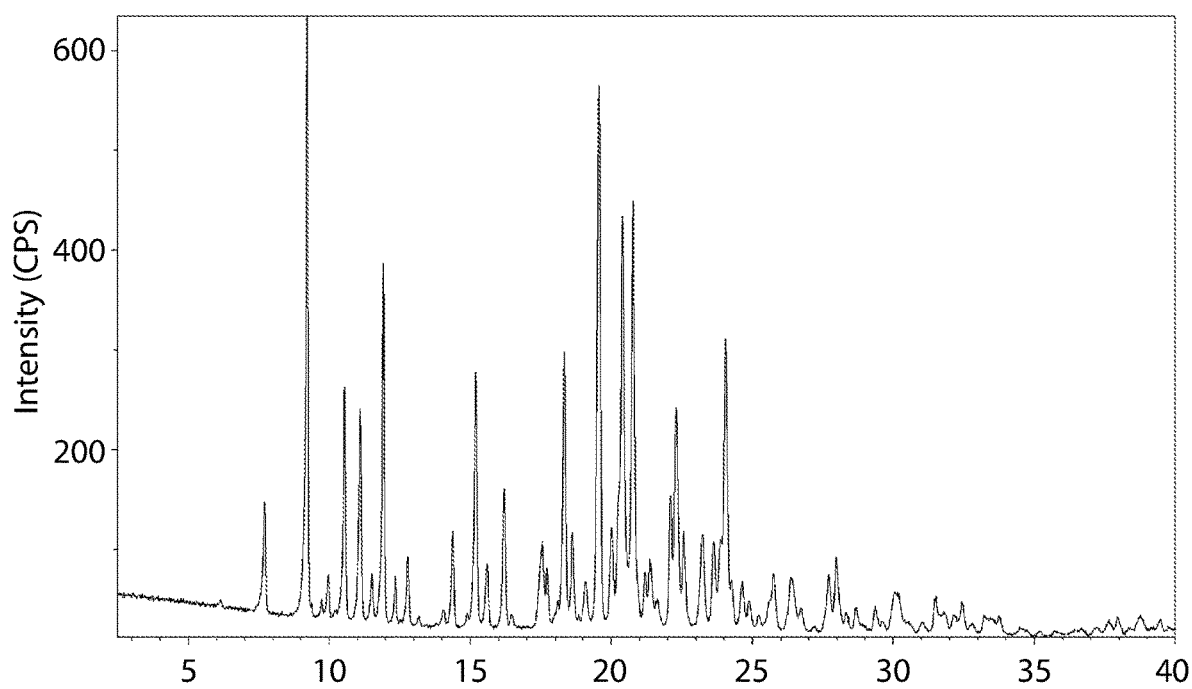
FIG. 21 shows an XRPD pattern for cannabidiol 4,4'-dipyridyl cocrystal Material B.

The XRPD pattern corresponding to cannabidiol 4,4'-dipyridyl Material B is shown in FIG. 21. As can be determined, the XPRD pattern of cannabidiol 4,4'-dipyridyl Material B in FIG. 21 differs from the XRPD pattern of cannabidiol starting material FIG. 1.

A pattern substantially the same as the pattern of cannabidiol:4,4'-dipyridyl shown in FIG. 21 may be used to characterize the cocrystal of cannabidiol 4,4'-dipyridyl Material B.

A smaller subset of the peaks identified for cannabidiol 4,4'-dipyridyl Material B in FIG. 21 may be used to characterize the cocrystal of cannabidiol 4,4'-dipyridyl Material B. For example, any one or more of the peaks identified at about °2θ may be used to characterize the cocrystal of cannabidiol:4,4'-dipyridyl Material B. For example, any one or more of the peaks at about 7.7, 9.2, 10.6, 11.1, 11.9, 15.2, 16.2, 18.3, 19.57, 20.4, 20.8, 22.1, 22.3, 24.1 degrees 2θ±0.2.

Also disclosed herein are methods for using the new cocrystal forms of cannabidiol for treating medical conditions such as, without limitation, convulsions and/or seizures, for example convulsions/seizures associated with epilepsy; psychiatric disorders (without limitation, schizophrenia, anxiety disorders, bipolar disorder); improving cognitive function, e.g., in subjects with schizophrenia; as an anti-inflammatory (e.g., without limitation, inflammatory bowel disease); pain (e.g., without limitation, chronic pain, neuropathic pain; nociceptive pain); hepatitis; spasticity in neurodegenerative diseases, such as multiple sclerosis; multiple sclerosis-related muscle spasms, restless leg syndrome, cachexia and anorexia; ocular hypertension in glaucoma; spasms in Tourette syndrome; reducing drug dependence such as cannabis use disorder, cocaine dependence, and opiate addiction; diabetes mellitus; graph versus host disease (GVHD); atherosclerosis; as a neuroprotective agent, cancers, such as without limitation solid tumors, hematological malignancies and cancers that have metastasized; anemias, Crohn's disease; ulcerative colitis; systemic lupus erythematosus (SLE); cutaneous lupus erythematosus; psoriasis; autoimmune uveitis; autoimmune hepatitis; hypersensitivity lung diseases; hypersensitivity pneumonitis; delayed-type hypersensitivity; Sjogren's disease; autoimmune thyroid disease; acquired immunodeficiency syndrome, sarcoidosis; rheumatoid arthritis; interstitial lung disease (ILD) (e.g., idiopathic pulmonary fibrosis, or ILD associated with rheumatoid arthritis or other inflammatory diseases); scleroderma; dermatitis (including atopic dermatitis and eczematous dermatitis); iritis, conjunctivitis; keratoconjunctivitis; idiopathic bilateral progressive sensorineural hearing loss; aplastic anemia; pure red cell anemia; idiopathic thrombocytopenia; polychondritis; Graves ophthalmopathy; amyotrophic lateral sclerosis (ALS); primary biliary cirrhosis; ileitis; chronic inflammatory intestinal disease, celiac disease; irritable bowel syndrome, Alzheimer's disease; prion associated disease; neurodegenerative disease, movement disorders, fatty liver; insomnia and other sleep disorders; posttraumatic stress syndrome; hypoxia-ischemia (including acute stroke); or other conditions reported or under investigation to be treatable with cannabidiol treatment comprising, or consisting essentially of, or consisting of administering to a subject in need of treatment an effective amount of the cannabidiol cocrystal.

As used herein, the term "subject" refers to an animal, typically a human (i.e., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey); other mammals such as rodents (mice, rats), cattle, pigs, horses, sheep, goats, cats, dogs; and/or birds, that will be or has been the object of treatment, observation, and/or experiment.

Terms such as "treating" or "treatment" or "to treat" or "alleviating" or "to alleviate" or to "ameliorate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented.

The term "therapeutically effective amount" as used herein refers to that amount of an embodiment of the composition or pharmaceutical composition being administered that will relieve to some extent one or more of the symptoms of the disease or condition being treated, and/or that amount that will prevent, to some extent, one or more of the symptoms of the condition or disease that the subject being treated has or is at risk of developing.

The dosage of the cannabidiol cocrystal to the patient can depend on the disease state or particular condition of the patient, as well as other clinical factors (e.g., weight and condition of the human or animal and the route of administration of the cannabidiol). The cannabidiol cocrystal can be administered between several times per day to a single treatment protocol. Optionally, the cannabidiol cocrystal can be delivered according to the disclosed processes either acutely, during a one-time intervention, or chronically, for instance using multiple administrations or optionally a single administration of a timed or sustained releases system. For example, the cannabidiol cocrystal can be administered to the patient via a drug delivery vehicle, such as a sustained release drug delivery vehicle. It is to be understood that the present disclosure has application for both human and veterinary use. The methods of the present invention contemplate single as well as multiple administrations, given either simultaneously or over an extended period of time. In addition, the cannabidiol cocrystal can be administered in conjunction with other forms of therapy.

In one embodiment, the cannabidiol cocrystal can be provided as a pharmaceutical composition using formulation methods known to those of ordinary skill in the art. These formulations can generally be administered by standard routes, such as non-parenterally, for example, buccally, sublingually, transdermally, via inhalation, or rectally. In other embodiments, the pharmaceutical composition is administered by direct injection into the subject, for example, parenterally, such as by injection or infusion. Still further the pharmaceutical composition can be administered by oral administration (e.g., in a pill, capsule form, as part of food, e.g. candy etc.).

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Compositions of the present invention can include additional agents, in addition to the cannabidiol cocrystal. Such agents can be active agents, providing direct benefit to the patient in addition to the treatment of condition provided by the cannabidiol cocrystal, or may be supporting agents, improving delivery, compatibility, or reactivity of other agents in the composition.

Compositions for parenteral delivery, e.g., via injection, of cannabidiol crystal can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the cannabidiol cocrystal. Proper fluidity may be maintained, for example, by the use of coating materials such as lecithin, by the maintenance of the required particle size in the case of dispersions and by the use of surfactants. These compositions may also include anti-oxidants, preservatives, wetting agents, emulsifying agents and dispersing agents.

Prevention of microorganism contamination may be ensured by the inclusion of various antibacterial and antifungal agents such as paraben, chlorobutanol, phenol, sorbic acid and the like. It may also be desirable to include isotonic agents such as sugars, sodium chloride and the like.

In one embodiment, the compositions can include pharmaceutically acceptable salts of the components therein, e.g., those that may be derived from inorganic or organic acids. Pharmaceutically acceptable salts are well known in the art. For example, S. M. Berge, et al. describes pharmaceutically acceptable salts in detail in *J. Pharmaceutical Sciences* (1977) 66:1 et seq., which is incorporated herein by reference. Pharmaceutically acceptable salts include the acid addition salts that are formed with inorganic acids such as, for example, hydrochloric or phosphoric acids, or such organic acids as acetic, tartaric, mandelic and the like. Salts formed with free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the cannabidiol or separately via reaction of a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemi sulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In one embodiment, the methods described herein can include use of timed release or sustained release delivery systems as are generally known in the art. Such systems can be desirable, for instance, in situations where long term delivery of the cannabidiol cocrystal to the subject is desired. According to this particular embodiment, a sustained-release matrix can include a matrix made of materials, usually polymers, which are degradable by enzymatic or acid/base hydrolysis or by dissolution. Once located within the subject, such a matrix can be acted upon by enzymes and body fluids. The sustained-release matrix can be chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Possible biodegradable polymers and their use are described, for example, in detail in Brem et al. (1991, *J. Neurosurg.* 74:441-6), which is hereby incorporated by reference in its entirety).

When an effective amount of the cannabidiol cocrystal is administered by intravenous or subcutaneous injection, the compositions can generally be in the form of a pyrogen-free, parenterally acceptable aqueous solution. The preparation of such parenterally acceptable solutions, having proper pH, isotonicity, stability, and the like, is within the skill in the art. A pharmaceutical composition for intravenous, cutaneous, or subcutaneous injection can contain, an isotonic vehicle such as Sodium Chloride Injection, Ringer's Injection, Dextrose Injection, Dextrose and Sodium Chloride Injection, Lactated Ringer's Injection, or other vehicle as known in the art. The treatment composition may also contain stabilizers, preservatives, antioxidants, or other additives known to those of skill in the art.

EXAMPLES

A. Experimental Methods:
1. Approximate Solubility

Weighed samples were treated with aliquots of a solvent or solvent mixture at RT. The mixtures were sonicated between additions to facilitate dissolution. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The solubility is expressed as "less than" if complete dissolution did not occur during the experiment. If complete dissolution was achieved as a result of only one aliquot addition, the solubility is expressed as "greater than."

B. Instrumental Techniques:

1. Indexing

Indexing is the process of determining the size and shape of the crystallographic unit cell given the peak positions in a diffraction pattern. The term gets its name from the assignment of Miller index labels to individual peaks. XRPD indexing serves several purposes. If all of the peaks in a pattern are indexed by a single unit cell, this is strong evidence that the sample contains a single crystalline phase. Given the indexing solution, the unit cell volume may be calculated directly and can be useful to determine their solvation states. Indexing is also a robust description of a crystalline form and provides a concise summary of all available peak positions for that phase at a particular thermodynamic state point. Indexing of XRPD pattern was done using TRIADS™ software (see U.S. Pat. No. 8,576,985). Space groups consistent with the assigned extinction symbol, unit cell parameters, and derived quantities are tabulated in the respective figures providing the indexing solution for each form.

2. Polarized Light Microscopy (PLM):

Samples were observed under a stereomicroscope with a first order red compensator with crossed polarizers at 0.8× to 10× objectives.

3. Proton Nuclear Magnetic Resonance Spectroscopy ($^1$H NMR):

The solution NMR spectrum was acquired with an Agilent DD2-400 spectrometerat a $^1$H Larmor frequency of 399.82 MHz. The sample was dissolved in deuterated chloroform. The spectrum was acquired with $^1$H pulse widths of 6.6 µs, a 2.5 second delay between scans, spectral widths of 6410.3 with 64102 data points, and 40 co-added scans. The free induction decay was processed using Varian VNMR 6.1C software with 262144 points and an exponential line broadening factor of 0.2 Hz to improve the signal-to-noise ratio.

4. X-Ray Powder Diffraction (XRPD):

a. PANalytical X'PERT Pro MPD Diffractometer-Transmission

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-µm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror.

5. Differential Scanning calorimetry (DSC):

DSC analysis was performed using a TA Instruments 2920 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., −30-250-10 means "from −30° C. to 250° C., at 10° C./min".

6. Fourier Transform Infrared Spectroscopy (FT-IR):

FT-IR data was acquired on Nicolet FTIR 6700 Fourier transform infrared spectrophotometer (Thermo Nicolet) equipped with an Ever-Glo mid/far IR source, a potassium bromide beamsplitter, and a deuterated triglycine sulfate detector. Wavelength verification was performed using NIST SRM 1921b (polystyrene). An attenuated total reflectance accessory (Thunderdome™, Thermo Spectra-Tech), with a germanium (Ge) crystal was used for data acquisition. Each spectrum represents 256 co-added scans collected at a spectral resolution of 4 cm−1. A background data set was acquired with a clean Ge crystal. A Log 1/R (R=reflectance) spectrum was obtained by taking a ratio of these two data sets against each other.

7. Thermogravimetric Analysis (TGA):

TG analysis was performed using a TA Instruments Discovery thermogravimetric analyzer with an IR furnace. Temperature calibration was performed using nickel and Alumel™. Each sample was placed in an aluminum pan. The sample was hermetically sealed, the lid pierced, then inserted into the TG furnace. The furnace was heated under nitrogen. The data acquisition parameters for each thermogram are displayed in the image in the Data section of this report. The acquisition scan rate is recorded in the thermogram header, while the heating range can be determined from the individual plot.

Results and Discussion:

Cannabidiol was analyzed by X-ray powder diffraction (XRPD) and $^1$H NMR spectroscopy.

The XRPD pattern of the starting material (FIG. 1) is composed of a crystalline material and compares favorably with the calculated XRPD pattern from the single crystal data for cannabidiol (Refcode: CANDOM10) in the Cambridge Structural Database).

The $^1$H NMR spectrum was collected as reference and found to be consistent with the structure of cannabidiol (data not shown).

A single endotherm was observed at approximately 70° C. (peak max) in the DSC data (data not shown). No significant weight loss was observed upon heating based on TGA (data not shown)

Kinetic solubility estimates of cannabidiol were determined in various solvents to aid in designing screening experiments (Tables 1 and 2). Solubilities were estimated by adding measured aliquots of solvent to weighed amounts of cannabidiol at room temperature (RT). Samples were sonicated in between aliquot additions and dissolution was judged by visual inspection. Discoloration of the solutions produced from solubility estimates in acetone, acetonitrile, DMA, DMF, p-dioxane, ethanol, IPOAc, MEK and methanol were observed after 1-3 days at room temperature.

TABLE 1

| Solvents | |
|---|---|
| Abbreviations/ Acronyms | Full Name/Description |
| ACN | Acetonitrile |
| DMA | Dimethylacetamide |
| DMF | Dimethylformamide |
| DCM | Dichloromethane |
| DMSO | Dimethyl sulfoxide |

TABLE 1-continued

Solvents

| Abbreviations/Acronyms | Full Name/Description |
| --- | --- |
| EtOH | Ethanol |
| EtOAc | Ethyl acetate |
| IPA | Isopropyl alcohol or 2-propanol |
| IPOAc | Isopropyl acetate |
| IPE | Diisopropyl ether |
| MIBK | Methylisobutyl ketone |
| MeOH | Methanol |
| MEK | Methyl ethyl ketone |
| MTBE | Methyl tert-butyl ether |
| NMP | N-Methyl-2-pyrrolidone |
| THF | Tetrahydrofuran |
| TFE | 2,2,2-Trifluoroethanol |

TABLE 2

Solubility Estimates for Cannabidiol at Ambient Temperature

| Solvent System | Solubility$^a$ |
| --- | --- |
| Acetone | 23 $^b$ |
| Acetonitrile | >50 $^b$ |
| Chloroform | 16 |
| Cyclohexane | 15 |
| DCM | 19 |
| Diethyl Ether | >57 |
| p-dioxane | >48 $^b$ |
| DMA | 28 $^b$ |
| DMF | 36 $^b$ |
| DMSO | 21 $^b$ |
| EtOAc | >46 |
| EtOH | 36 $^b$ |
| Heptane | 10 |
| IPA | 14 |
| IPOAc | >68 $^b$ |
| MEK | >55 $^b$ |
| MeOH | >57 $^b$ |
| MIBK | >59 |
| MTBE | 34 |
| NMP | 29 |
| TFE | <1 |
| THF | >71 |
| Butanol | 9 |
| Water | <1 |
| Octanol | 13 |

$^a$Solubilities are calculated based on the total solvent used to give a solution; actual solubilities may be greater because of the volume of the solvent portions used or a slow rate of dissolution.
Values are rounded to the nearest whole number.
If dissolution did not occur as determined by visual assessment after the addition of the first aliquot, the value is reported as "<".
If dissolution occurred as determined by visual assessment after the addition of the first aliquot, the value is reported as ">".
$^b$ Color change of solution at RT observed after completion of solubility estimates B.

Cocrystal Screen

A cocrystal screen of cannabidiol was performed using primarily pharmaceutically acceptable coformers. Sixty-eight (68) experiments targeting cocrystals of cannabidiol were conducted using 34 coformers. Cannabidiol is reported to be highly chemically reactive (Mechoulam, R. and Janus, L, Cannabidiol: an overview of some chemical and pharmacological aspects. Part I; chemical aspects (2002) Chem Phys Lipids 121(1-2):35-43). For example, cannabidiol in base in the presence of oxygen is reported to oxidize to monomeric and dimeric hydroquinones (id.) The anions of the oxidized compound have a deep violet color and is the basis of the Beam reaction used for the identification of cannabis (id.). Attempts to form cocrystals of cannabidiol with pharmaceutically acceptable bases such as imidazole to potentially exploit the O—H . . . N hydrogen bond, resulted in discoloration of the solution, possibly as a result of the Beam reaction. Thus, the pKa's of the bases used were taken into consideration in tailoring experimental conditions. Compounds that were less basic such as those containing aromatic nitrogen were evaluated to exploit the O—H . . . N hydrogen bond. Experiments were set up at approximately 1:1, 2:1, or 1:2 API: coformer ratio with additional experiments performed using an excess amount of coformer. Experiments were conducted using a variety of crystallization techniques including cooling, evaporation, slurrying, and solvent assisted grinding. Solids resulting from cocrystal screening experiments were typically analyzed by polarized light microscopy (PLM) and X-ray powder diffraction (XRPD). The XRPD patterns of the isolated solids were compared to that of known forms of cannabidiol and coformer.

The majority of experiments conducted targeting cocrystals of Cannabidiol resulted in cannabidiol, coformer, physical mixtures of cannabidiol and coformer, gels, oils, or discolored solutions.

Four cocrystals of cannabidiol were discovered: cannabidiol L-proline Form A, cannabidiol D-proline Form A, cannabidiol tetramethylpyrazine Material A and cannabidiol 4,4'-dipyridyl Material A (Table 3). Additionally, a unique crystalline material, designated 4,4'-dipyridyl Material B, resulted after cannabidiol 4,4'Material A was exposed to 95% relative humidity (RH) for 1 week at room temperature (RT).

TABLE 3

Summary of Unique Cocrystals obtained in Cannabidiol Cocrystal Screen

| Coformer | Characterization | Comment |
| --- | --- | --- |
| L-Proline | XRPD with indexing, 1H NMR, DSC, TGA, FT-IR, aqueous | 1:1 cocrystal, unsolvated/anhydrous |
| D-Proline | XRPD with indexing, 1H NMR, DSC, TGA, FT-IR, aqueous | 1:1 cocrystal, unsolvated/anhydrous |
| Tetramethyl-pyrazine | XRPD, 1H NMR, DSC, TGA, FT-IR, | Approximately 1:1 cocrystal |
| 4,4'-Dipyridyl | XRPD, 1H NMR, DSC, TGA, FT-IR, | Approximately 1:1 cocrystal |

1. Cannabidiol:L-Proline (1:1) Form A:

A unique crystalline material was identified from experiments targeting a cocrystal of cannabidiol with L-proline. The potential lead with L-proline was obtained from several different experimental conditions involving different ratios of cannabidiol and L-proline in the presence of MeOH. Evaporation of a solution containing cannabidiol and excess L-proline in MeOH resulted in a unique crystalline material that was isolated as a mixture with L-proline based on XRPD (FIG. 2). Solvent assisted grinding of Cannabidiol and L-proline with MeOH and evaporation of MeOH solutions containing Cannabidiol and L-proline (1:1 and 2:1 mole ratio) also resulted in the same unique crystalline material. Characterization of cannabidiol:L-proline (1:1) Form A is shown in Table 4.

The XRPD pattern of the sample resulting from the evaporation experiment targeting a 1:1 cocrystal of cannabidiol and L-proline was successfully indexed. Successful indexing indicates the material is composed primarily or exclusively of a single crystalline phase. The indexed volume is consistent with a cannabidiol: L-proline 1:1 cocrystal with possible water or methanol present.

Figure 6:
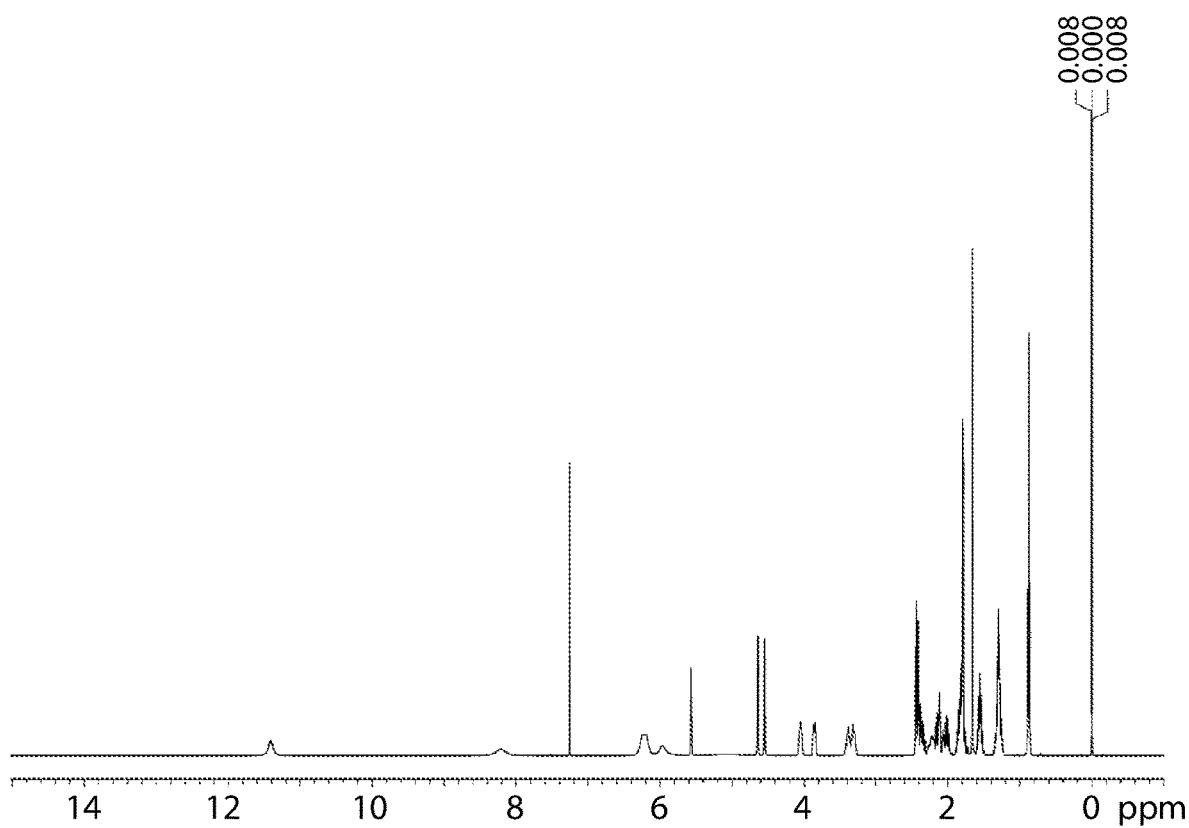
FIG. 6 shows a proton nuclear magnetic resonance spectrum of cannabidiol L-Proline Form A.

The ¹H NMR spectrum of the sample contained cannabidiol and L-proline in an approximate 1:1 mole ratio suggesting a cannabidiol L-proline 1:1 cocrystal (FIG. 6).

The DSC thermogram shows a single sharp endotherm with an onset at about 146.4° C. and peak maximum at 147.8° C. (FIG. 3). No significant weight loss is observed in the TGA thermogram suggesting the sample is likely unsolvated/anhydrous. Approximately 0.1 weight % loss is observed between about 28° C. and 160° C. (beyond the melt) (FIG. 4).

The aqueous solubility of cannabidiol L-proline Form A was estimated to be <1 mg/ml using an aliquot addition method.

A sample of cannabidiol L-proline Form A was exposed to 95% RH at RT for 1 week and no change in physical form was observed based on XRPD (data not shown).

Cannabidiol L-proline Form A was stored at about 2-8° C. for about 15 weeks, and the sample was analyzed by XRPD. No change in physical form was observed after storage based on XRPD (data not shown).

Method of Preparing Cannabidiol Cocrystal:

Cannabidiol (87.76 mg, 0.28 mmol) and L-proline (33.8, 0.29 mmol) mg was dissolved in methanol (350 μL) at room temperature (RT). The clear solution was stirred at RT for approximately 3 hours. The solution was allowed to evaporate under nitrogen for 1 day.

TABLE 4

CHARACTERIZATION OF CANNABIDIOL:L-PROLINE (1:1) FORM A

| Technique | Results |
| --- | --- |
| PLM1 | B/E, fines, needles, agglomerates |
| XRPD | Crystalline, successfully indexed |
| ¹H NMR | Consistent with Cannabidiol:L-Proline (1:1) Form A |
| DSC | Endotherm: 146.4° C. (onset), 147.8° C. (peak maximum) |
| TGA | 0.1% wt loss up to 160.0° C. |
| FT-IR | collected as reference |

The FT-IR spectrum of cannabidiol L-proline Form A was collected as reference and is shown in FIG. 5.
The aqueous solubility of cannabidiol L-proline Form A was estimated to be <1 mg/ml using an aliquot addition method
2. Cannabidiol D-Proline Form A:

Cannabidiol D-Proline Form A was produced under two conditions: solvent assisted grinding of cannabidiol and D-proline with MeOH produced a unique material by XRPD (FIG. 7); and evaporation of a MeOH solution containing equimolar amounts of cannabidiol and D-proline. Characterization of cannabidiol D-proline Form A is presented in Table 5.

TABLE 5

CHARACTERIZATION OF CANNABIDIOL D-PROLINE FORM A

| Technique | Results |
| --- | --- |
| PLM | B/E, fines, needles, agglomerates |
| XRPD | Crystalline, successfully indexed, designated cannabidiol D-proline Form A |
| TGA[a] | 0.1% wt loss up to 110.0° C. |
| FT-IR | Collected as reference |
| Aqueous solubility estimate | <1 mg/mL |

TABLE 5-continued

CHARACTERIZATION OF CANNABIDIOL D-PROLINE FORM A

| Technique | Results |
| --- | --- |
| XRPD of LIMS 472843 after exposure to 95% RH at RT for 1 week | Crystalline, Cannabidiol D-Proline Form A |
| XRPD | cannabidiol D-proline Form A + minor peaks at ~9.8° and ~18° (2θ) |
| DSC[a] | Sharp endotherm: 154.3° C. (onset), 155.5° C. (peak max) |
| ¹H NMR | Consistent with cannabidiol with D-proline in 1:1 mol:mol ratio, based on peak at 4.06 ppm |

[a]Temperatures are reported to the nearest tenth of a degree.

Figure 11:
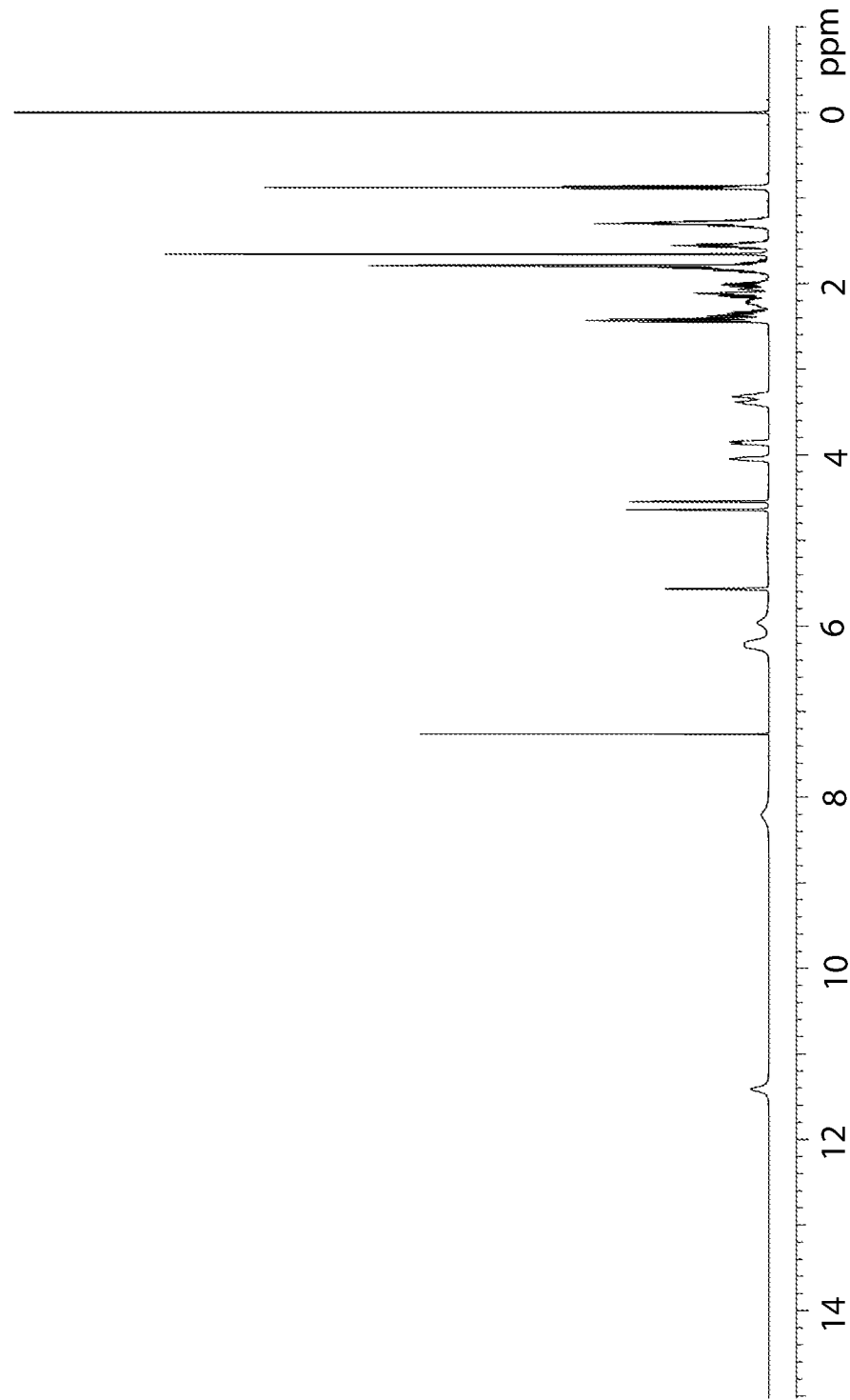
FIG. 11 shows a proton nuclear magnetic resonance spectrum of cannabidiol D-proline cocrystal Form A.

The ¹H NMR spectrum of cannabidiol D-proline Form A is consistent with cannabidiol and D-proline in a 1:1 mole ratio based on the peak at 4.06 ppm (FIG. 11). No residual organic solvent was observed.

No significant weight loss is observed in the TGA thermogram up to the, suggesting the sample is likely unsolvated/anhydrous (FIG. 9)

The aqueous solubility of cannabidiol D-proline Form A was estimated to be <1 mg/ml using an aliquot addition method.

The FT-IR spectrum of cannabidiol D-proline Form A was collected as a reference and is shown in FIG. 10.

DSC thermogram of cannabidiol D-proline Form A shows a single endotherm with an onset at about 154° C. (FIG. 8)
Preparation of Cocrystal of Cannabidiol and D-proline Form A:

Methanol (0.9 mL) was added to Cannabidiol (92.4 mg, 0.29 mmol) and D-proline (34.8 mg, 0.30 mmol) to produce a clear solution. The solution was evaporated under nitrogen for 3 days.
3. Cannabidiol Tetramethylpyrazine Material A:

Cannabidiol tetramethylpyrazine Material A was isolated as a disordered material from solvent assisted grinding of equimolar amounts of cannabidiol and tetramethylpyrazine (TMP) in a 1:1 with MeOH. A second solvent assisted grinding experiment containing cannabidiol and TMP in a 1:2 mole ratio resulted in the same disordered material with additional peaks present. Solids isolated from the experiment containing equimolar amount of cannabidiol and TMP were analyze by XRPD (FIG. 12), ¹H NMR, DSC, and FT-IR spectroscopy. Additionally, a visual estimate of the aqueous solubility was conducted and solids of cannabidiol tetramethylpyrazine Material A were exposed to 95% RH then analyzed by XRPD.

Characterization of cannabidiol tetramethylpyrazine Material A is presented in Table 6.

Figure 15:
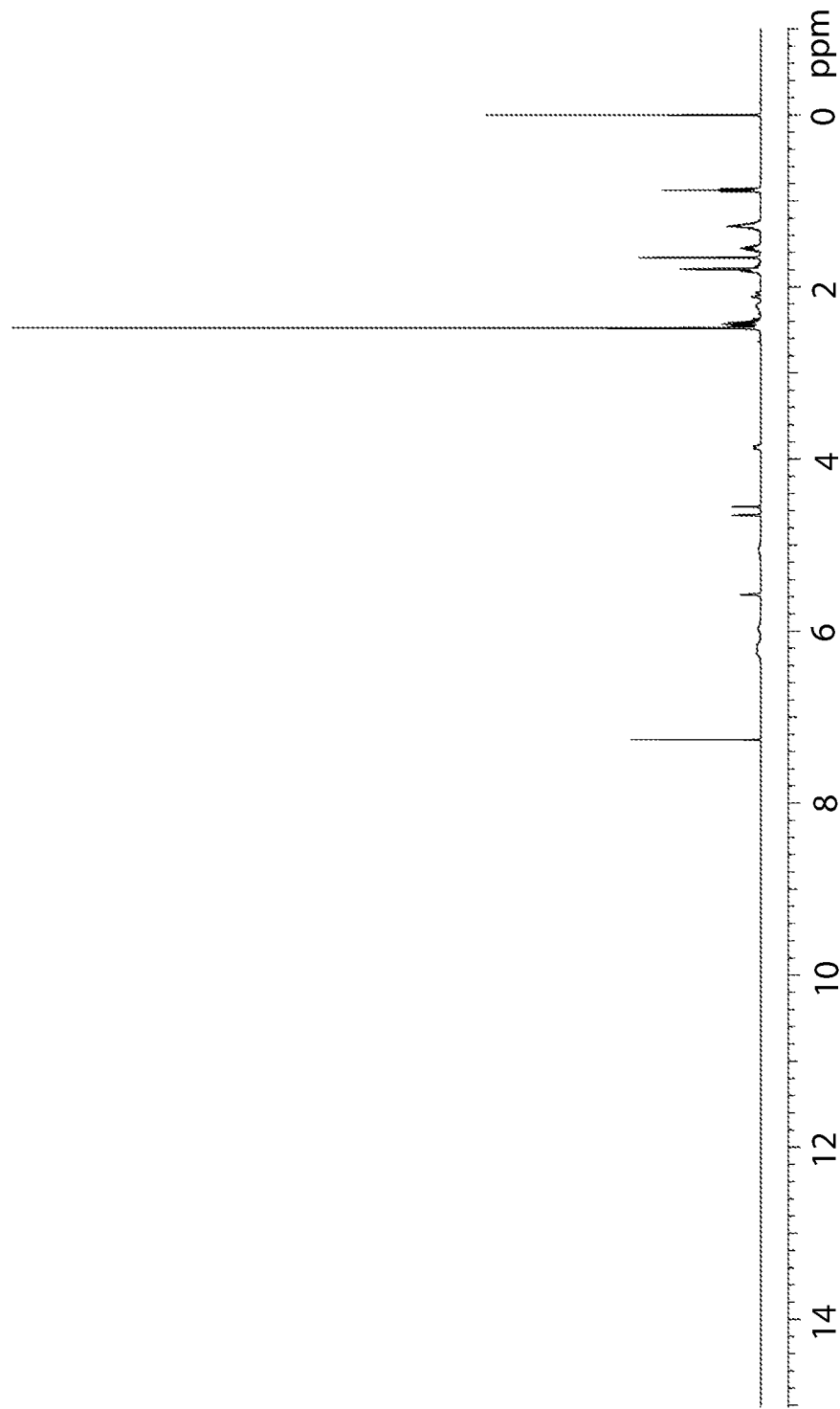
FIG. 15 shows a proton nuclear magnetic resonance spectrum of cannabidiol tetramethylpyrazine cocrystal.

The ¹H NMR spectrum of the sample is consistent with the chemical structure of cannabidiol and contains approximately 0.9 mole TMP per mole of cannabidiol (FIG. 15). No decomposition of cannabidiol is observed based on the ¹H NMR data.

The DSC thermogram of cannabidiol TMP Material A shows a single sharp endotherm with an onset at 90° C. and a peak maximum at 93° C., likely attributed to the melting of the cocrystal (FIG. 13).

Figure 14:
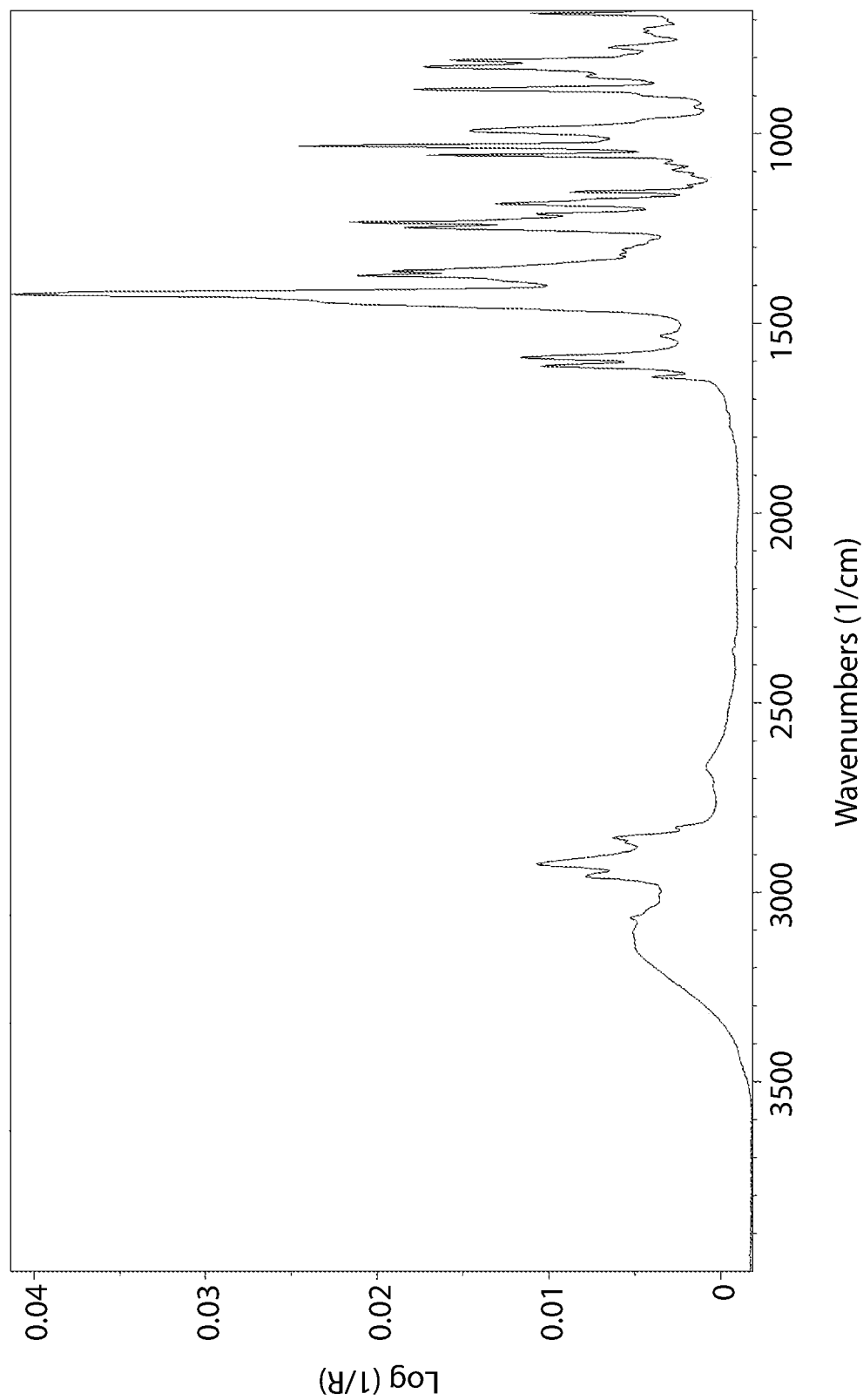
FIG. 14 shows an infrared spectrum of cannabidiol tetramethylpyrazine cocrystal.

The FT-IR spectrum of cannabidiol TMP Material A was collected as reference (FIG. 14).

The aqueous solubility of cannabidiol TMP Material A was estimated to be <1 mg/mL using an aliquot addition method.

A sample of cannabidiol TMP Material A was exposed to 95% RH at RT for 1 week and no change in physical form was observed based on XRPD (data not shown).

Due to insufficient sample, solids obtained from the cannabidiol: TMP (1:2) experiment, consistent with cannabidiol TMP Material A with additional peaks of cannabidiol, was used for additional thermal characterization. Two endotherms were observed in the DSC data, one endotherm with an onset at 63° C. and a peak maximum at 65° C., likely attributed to melting of cannabidiol, followed by a second endotherm with a peak maximum at 87° C., attributed with melting/decomposition of the cocrystal (data not shown). The TGA thermogram exhibited a weight loss of 0.1% between 24 and 45° C.

Preparation of tetramethylpyrazine Material A:

Cannabidiol (51.0 mg, 0.16 mmol) and tetramethylpyrazine (22.1 mg, 0.16 mmol) were combined and contacted with a small quantity of MeOH producing a thick paste. The sample was lightly ground in an agate mortar/pestle and generated a white powder. Solids were collected and analyzed.

TABLE 6

CHARACTERIZATION OF CANNABIDIOL TETRAMETHYLPYRAZINE MATERIAL A

| Technique | Results |
|---|---|
| XRPD | Disordered crystalline, designated cannabidiol tetramethylpyrazine (TMP) Material A |
| DSC[a] | Endotherm: 89.9° C. (onset), 92.8° C. (peak max) |
| FT-IR | Collected as reference |
| Aqueous solubility estimate | <1 mg/mL |
| XRPD of LIMS 472818 after exposure to 95% RH at RT for 1 week | Crystalline, Cannabidiol Tetramethylpyrazine Material A |
| $^1$H-NMR | No decomposition detected. Consistent with cannabidiol:tetramethylpyrazine in ~1:0.9 mol:mol ratio |
| XRPD | Disordered crystalline (cannabidiol TMP Material A) + additional peaks |
| TGA[a] | 0.1% wt loss up to 45.4° C. |
| DSC[a] | Endotherm: 62.6° C. (onset), 65.1° C. (peak max) Endotherm: 87.2° C. (peak max) |

[a]Temperatures are reported to the nearest tenth of a degree.

4. Cannabidiol 4,4'-Dipyridyl Material A:

Cannabidiol 4,4'-dipyridyl Material A was identified from solvent assisted grinding experiments involving cannabidiol with equimolar amounts as well as two molar equivalents of 4,4-dipyridyl in the presence of MeOH (XRPD, FIG. 16). Characterization of cannabidiol 4,4'-dipyridyl Material A is summarized in Table 7.

Figure 20:
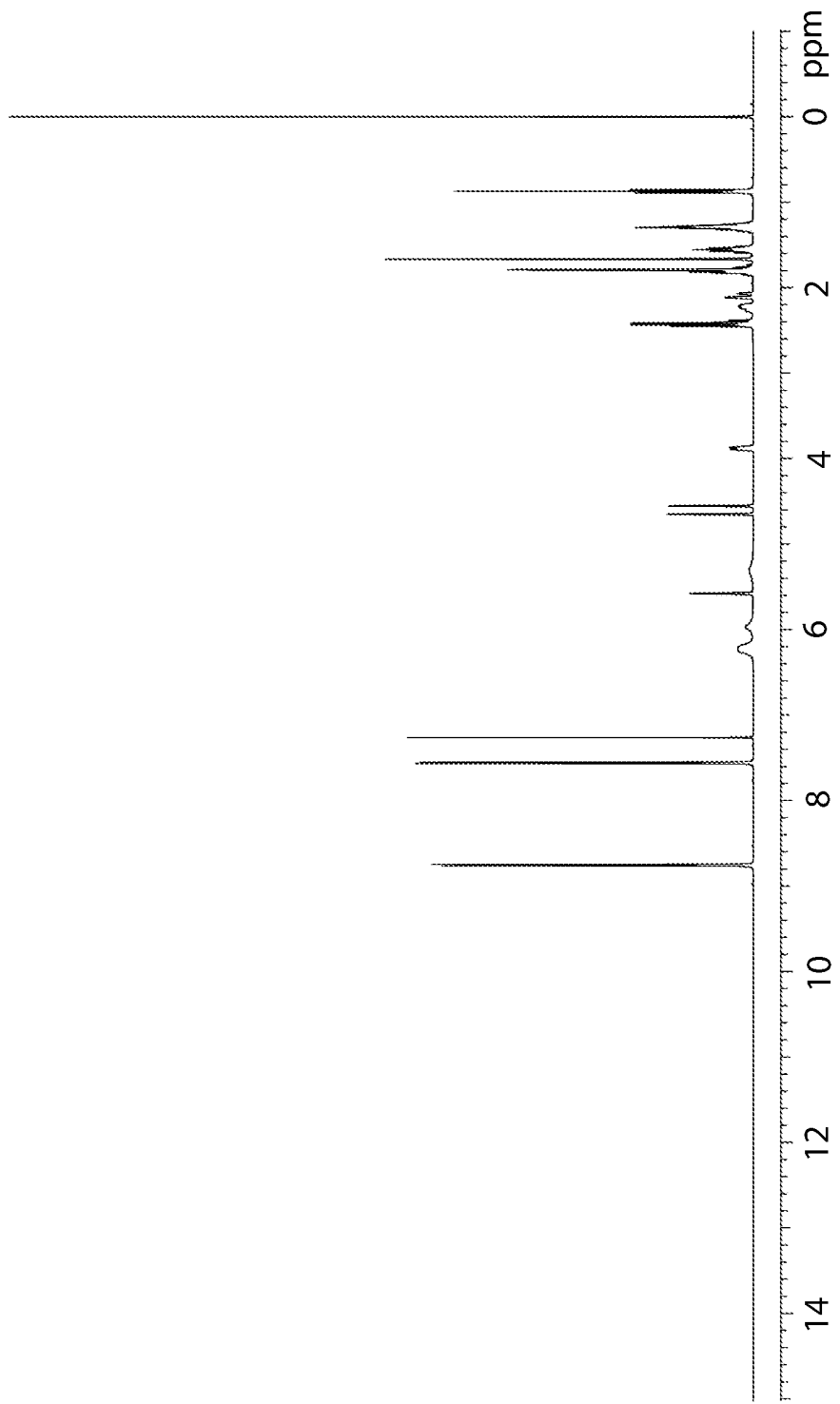
FIG. 20 shows a proton nuclear magnetic resonance spectrum of cannabidiol 4,4'-dipyridyl cocrystal.

The $^1$H NMR spectrum of the sample is consistent with the chemical structure of cannabidiol and is generally consistent with cannabidiol and 4,4'-dipyridyl in an approximately 1:0.9 mole ratio (FIG. 20). No decomposition of cannabidiol is observed based on the $^1$H NMR data.

Figure 17:
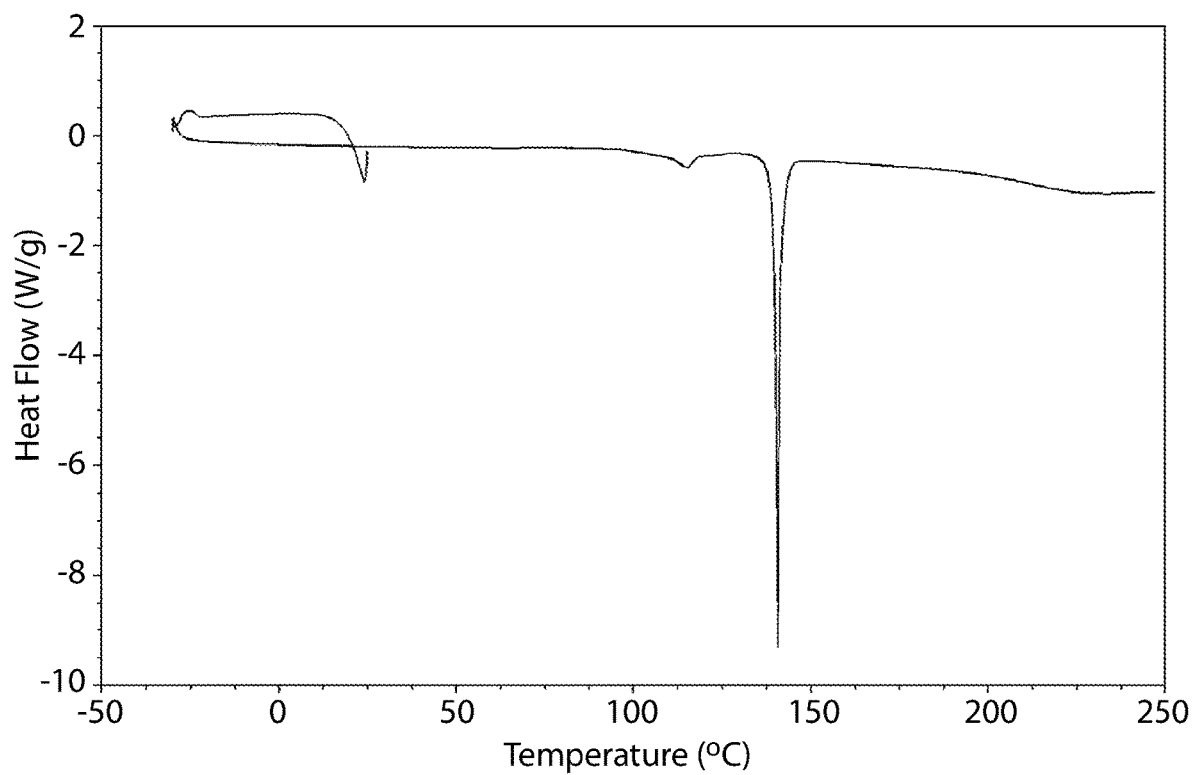
FIG. 17 shows a differential scanning calorimetry thermogram for cannabidiol 4,4'-dipyridyl cocrystal.
Figure 18:
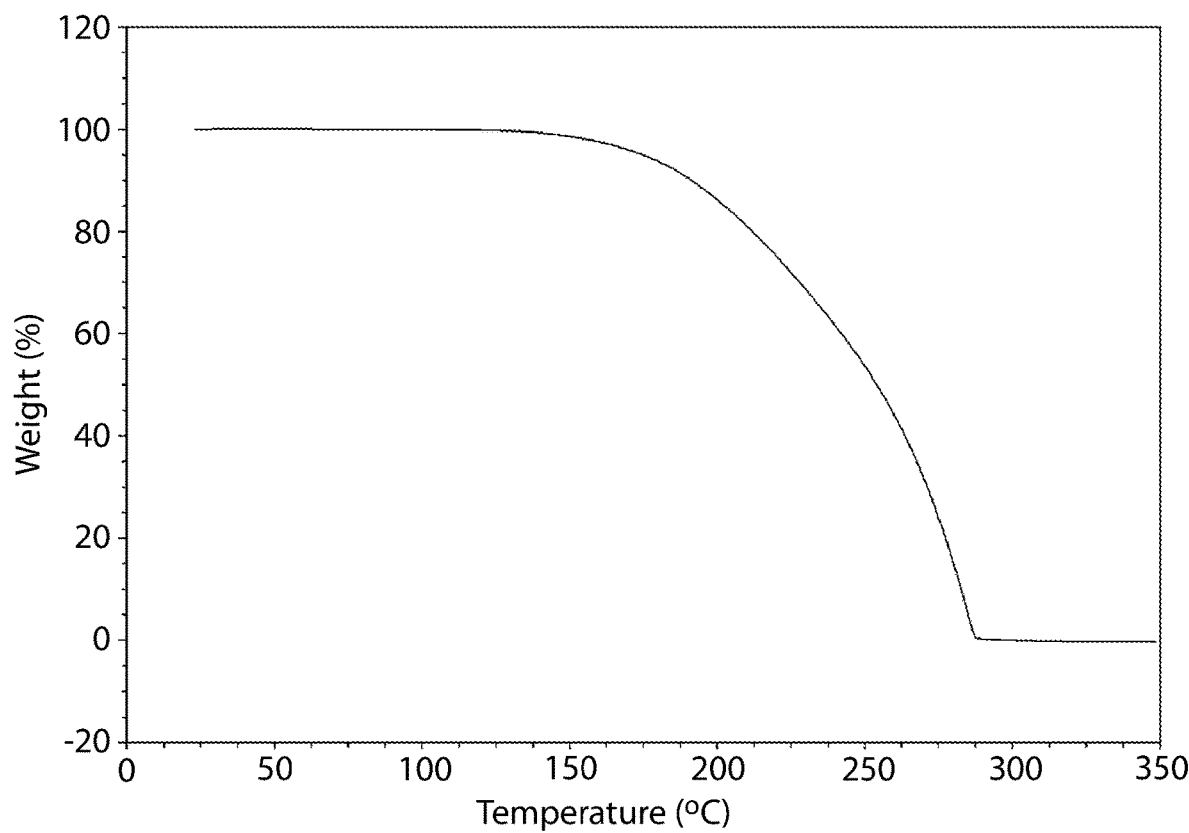
FIG. 18 shows a thermogravimetric thermogram for cannabidiol 4,4'-dipyridyl cocrystal.

The DSC thermogram exhibits a broad feature at 114.8° C. (peak max), followed by a sharp endotherm at 140.7° C. (peak max) that is likely due to melting (FIG. 17). No significant weight loss is observed in the TGA thermogram upon heating up to the likely melt (FIG. 18).

Figure 19:
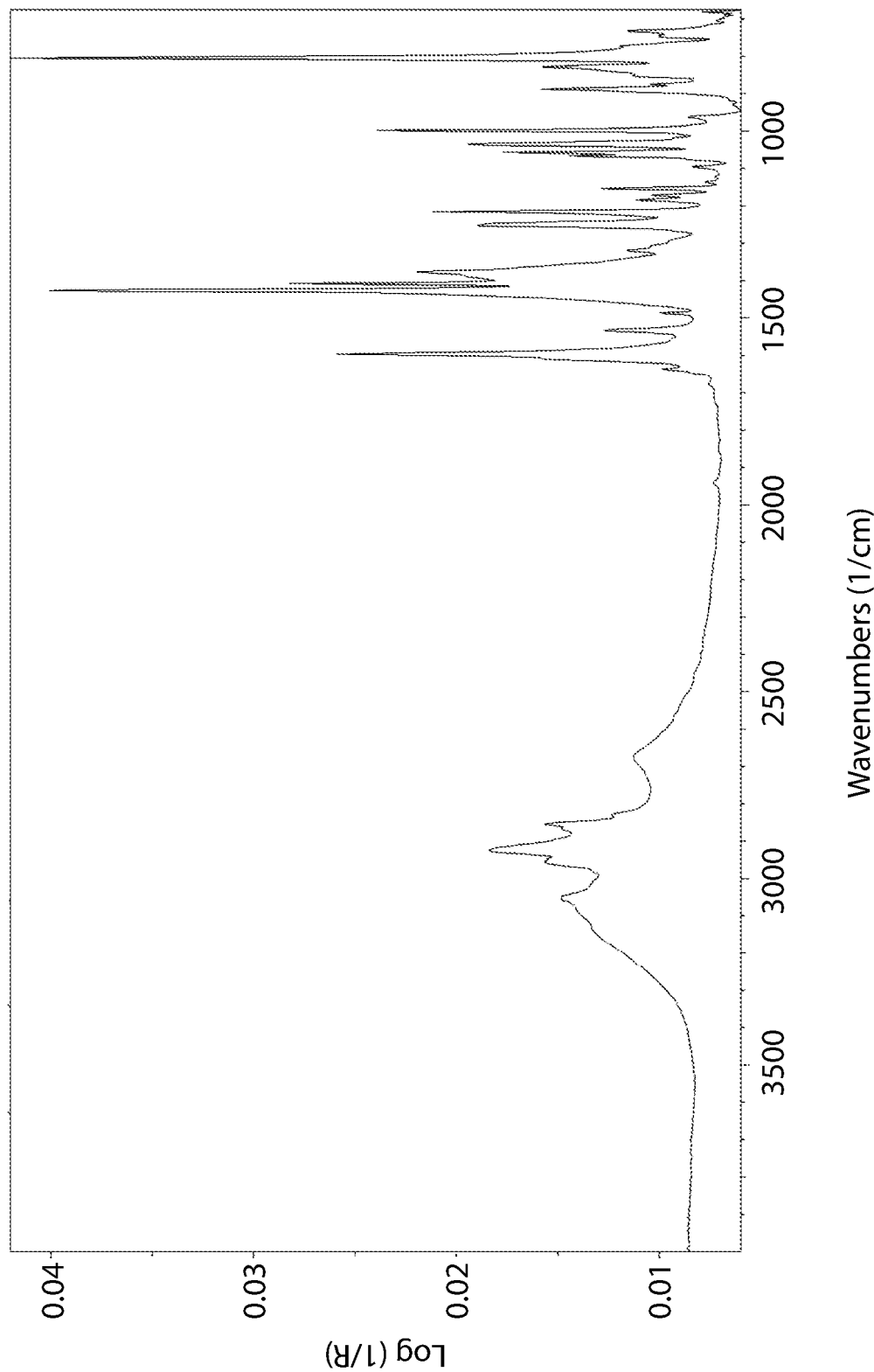
FIG. 19 shows an infrared spectrum of cannabidiol 4,4'-dipyridyl cocrystal.

The FT-IR spectrum of cannabidiol 4,4'-dipyridyl Material A was collected as reference (FIG. 19).

The aqueous solubility of cannabidiol 4,4'-dipyridyl Material A was estimated to be <1 mg/mL using an aliquot addition method.

A sample of cannabidiol 4,4'-dipyridyl Material A was exposed to 95% RH at RT for 1 week and resulted in a unique crystalline material by XRPD (Material B) (FIG. 21), indicating a change in physical form had occurred under the stressed conditions.

Preparation of Cannabidiol 4,4-Dipyridyl Material A:

Cannabidiol (55.4 mg, 0.18 mmol) and 4,4'-dipyridyl (27.4 mg, 0.18 mmol) were combined and contacted with a small quantity of MeOH producing a thick paste. The sample was lightly ground in an agate mortar/ pestle and generated a white powder. Solids were collected and analyzed.

A comparison of the physical properties of the discovered cocrystals and cannabidiol are presented in Table 8.

TABLE 7

CHARACTERIZATION OF CANNABIDIOL 4,4-DIPYRIDYL MATERIAL A

| Technique | Results |
|---|---|
| XRPD | Crystalline, designated cannabidiol 4,4'-Dipyridyl Material A |
| DSC[a] | Broad endotherm: 106.5° C. (onset), 114.8° C. (peak max) Sharp endotherm: 139.6° C. (onset), 140.7° C. (peak max) |
| TGA[a] | No weight loss 23.0 to 75.0° C. |
| FT-IR | Collected as reference |
| Aqueous solubility estimate | <1 mg/mL |
| $^1$H-NMR | No decomposition detected. Consistent with cannabidiol:4,4'-dipyridyl in ~1:0.9 mol:mol ratio |
| XRPD of LIMS 472819 after exposure to 95% RH at RT for 1 week | Unique crystalline material, 4,4'-Dipyridyl Material B |

[a]Temperatures are reported to the nearest tenth of a degree.

TABLE 8

COMPARISON OF THE PHYSICAL PROPERTIES OF CANNABIDIOL AND ITS COCRYSTALS

| | Cannabidiol | Cocrystal | | | |
|---|---|---|---|---|---|
| Analysis | Starting | L-Proline | D-Proline | TMP | 4,4-Dipyridyl |
| XRPD | Crystalline, single crystal structure | Crystalline, successfully indexed | Crystalline, successfully indexed | Disordered crystalline | Crystalline |

TABLE 8-continued

COMPARISON OF THE PHYSICAL PROPERTIES OF
CANNABIDIOL AND ITS COCRYSTALS

| | Cannabidiol | Cocrystal | | | |
|---|---|---|---|---|---|
| Analysis | Starting | L-Proline | D-Proline | TMP | 4,4-Dipyridyl |
| DSC | Endotherm: 66.6° C. (onset), 69.9° C. (peak max) | Sharp endotherm: 146.4° C. (onset), 147.8° C. (peak max) | Sharp endotherm: 154.3° C. (onset), 155.5° C. (peak max)$^a$ | Endotherm: 89.9° C. (onset), 92.8° C. (peak max) | Broad endotherm: 106.5° C. (onset), 114.8° C. (peak max) Sharp endotherm: 139.6° C. (onset), 140.7° C. (peak max) |
| TGA | No weight loss up | 0.1% weight loss up to 160° C. | 0.1% weight loss up to 110° C. | 0.1% weight loss up to 45° C.$^b$ | No weight loss 23.0 to 75.0° C. |
| $^1$H-NMR | Corresponds to structure | Consistent with cannabidiol:L-proline 1:1 mol | Consistent with cannabidiol:D-proline in 1:1 | Consistent with cannabidiol:TMP in ~1:0.9 | Consistent with cannabidiol:4,4'-dipyridyl in ~1:0.9 mol:mol ratio |
| FT-IR | — | Collected as reference | Collected as reference | Collected as reference | Collected as reference |
| Aqueous solubility | <1 mg/mL | <1 mg/mL | <1 mg/mL | <1 mg/mL | <1 mg/mL |
| XRPD after 95% RH at RT for 1 week | — | Crystalline, cannabidiol L-proline Form A, No physical form change | Crystalline, cannabidiol D-proline Form A, no physical form change | Crystalline, cannabidiol TMP Material A, no physical form change | Crystalline, unique, physical form change occurred |

$^a$Minor peaks attributed to cannabidiol based on XRPD were present in material tested for this analysis
$^b$Additional peaks observed by XRPD in material tested for this analysis

What is claimed is:

1. A solid form comprising cannabidiol and the coformer tetramethylpyrazine, wherein the solid form has an x-ray diffraction pattern comprising one or more peaks at about 9.1, 14.6, 18.3, and 19.6 degrees 2θ±0.2.

2. The solid form of claim 1 having an x-ray powder diffraction pattern substantially similar to FIG. 12.

3. The solid form of claim 1, wherein the molar ratio of cannabidiol to tetramethylpyrazine is about 1:1.

4. The solid form of claim 1, which is crystalline.

5. The solid form of claim 1, which is a cocrystal.

6. The solid form of claim 1 having a DSC thermogram with a peak onset of approximately 89.9° C. or a peak maximum at about 92.8° C.

7. The solid form of claim 6 having a DSC thermogram which is substantially similar to the DSC thermogram of FIG. 13.

8. A pharmaceutical composition comprising the solid form of claim 1.

9. The pharmaceutical composition of claim 8, further comprising a pharmaceutically acceptable excipient or carrier.

* * * * *